US010687543B2

(12) United States Patent
Griffiths et al.

(10) Patent No.: US 10,687,543 B2
(45) Date of Patent: *Jun. 23, 2020

(54) PROBIOTIC BACTERIAL MOLECULES AND THEIR USE IN METHODS TO TREAT/PREVENT INFECTION BY HARMFUL BACTERIA AND TO PROVIDE NUTRITIONAL HEALTH

(71) Applicant: UNIVERSITY OF GUELPH, Guelph (CA)

(72) Inventors: Mansel Griffiths, Rockwood (CA); Maira Medellin-Pena, Kitchener (CA); Veronique Delcenserie, Mississauga (CA)

(73) Assignee: University of Guelph, Guelph (CA)

( * ) Notice: Subject to any disclaimer, the term of this patent is extended or adjusted under 35 U.S.C. 154(b) by 33 days.

This patent is subject to a terminal disclaimer.

(21) Appl. No.: 15/696,255

(22) Filed: Sep. 6, 2017

(65) Prior Publication Data

US 2018/0000126 A1 Jan. 4, 2018

Related U.S. Application Data

(63) Continuation of application No. 13/001,328, filed as application No. PCT/CA2009/000901 on Jun. 26, 2009.

(60) Provisional application No. 61/076,581, filed on Jun. 27, 2008.

(51) Int. Cl.
| | |
|---|---|
| *A61K 38/07* | (2006.01) |
| *A61K 38/08* | (2019.01) |
| *C07K 5/107* | (2006.01) |
| *C07K 5/117* | (2006.01) |
| *A61P 31/04* | (2006.01) |
| *A23K 20/195* | (2016.01) |
| *A61K 35/744* | (2015.01) |
| *A61K 35/745* | (2015.01) |
| *A61K 35/747* | (2015.01) |
| *C07K 5/113* | (2006.01) |
| *C07K 7/06* | (2006.01) |
| *C07K 14/335* | (2006.01) |
| *A23L 33/135* | (2016.01) |
| *A23K 10/18* | (2016.01) |

(52) U.S. Cl.
CPC ............ *A23K 20/195* (2016.05); *A23K 10/18* (2016.05); *A23L 33/135* (2016.08); *A61K 35/744* (2013.01); *A61K 35/745* (2013.01); *A61K 35/747* (2013.01); *A61K 38/07* (2013.01); *A61K 38/08* (2013.01); *C07K 5/1016* (2013.01); *C07K 5/1021* (2013.01); *C07K 7/06* (2013.01); *C07K 14/335* (2013.01); *Y02A 50/473* (2018.01); *Y02A 50/481* (2018.01)

(58) Field of Classification Search
None
See application file for complete search history.

(56) References Cited

U.S. PATENT DOCUMENTS

| | | | |
|---|---|---|---|
| 6,476,209 | B1 | 11/2002 | Glenn et al. |
| 6,746,672 | B2 | 6/2004 | O'Sullivan et al. |
| 2004/0115177 | A1 | 6/2004 | Harris et al. |
| 2004/0161422 | A1 | 8/2004 | Ranganathan |
| 2006/0269523 | A1 | 11/2006 | Stern et al. |
| 2007/0161780 | A1 | 7/2007 | Georgiades et al. |
| 2015/0044188 | A1 | 2/2015 | Griffiths |

FOREIGN PATENT DOCUMENTS

| | | |
|---|---|---|
| WO | 2007/057872 | 5/2007 |
| WO | 2007/096855 | 8/2007 |
| WO | 2009/118243 | 10/2009 |
| WO | 2009/155711 | 12/2009 |

OTHER PUBLICATIONS

Hendrickson et al. Remington: The Science and Practice of Pharmacy, 21st Ed.; Lippincott Williams & Wilkins: Philadelphia, PA, 2005: pp. 828-831.
De Vuyst L and Leroy F. Bacteriocins from lactic acid bacteria: production, purification and food applications. Journal of Molecular Microbiology and Biotechnology. 2007; 13: 194-199.
Medillin-Pena MJ et al. Probiotics affect virulence-related gene expression in *Escherichia coli* O157:H7. Appl. Environ. Microbiol. 2007; 73: 4259-67.
Cheikyoussef A et al. Antimicrobial proteinaceous compounds obtained from Bifidobacteria: from production to their application. International Journal of Food Microbiology. Jul. 31, 2008; 125(3): 215-222.
Cheikyoussef A et al. Study of the Inhibition effects of Bifidobacterium supermatants towards growth of Bacillus cereus and *Eschelichia coli*. Internation Journal of Dairy science, 2007; 2(2): 116-125.
Vinderola G et al. Milk fermented by Lactobacillus helveticus R389 and Its non-bacterial fraction confer enhanced protection against *Salmonella enteritidis* serovar Typhimurium infection in mice. Immunobiology. 2007; 212: 107-118.

(Continued)

*Primary Examiner* — Michelle F. Paguio Frising
(74) *Attorney, Agent, or Firm* — Myers Bigel, P.A.

(57) ABSTRACT

This invention provides isolated and characterized secreted molecules from probiotic bacteria for use in compositions and methods for the treatment and/or prevention of infection by harmful pathogenic bacteria. The isolated secreted molecules can also be used in nutritional or medical food products which provide probiotics to the gastrointestinal tract of a mammal.

12 Claims, 9 Drawing Sheets

Specification includes a Sequence Listing.

(56) References Cited

OTHER PUBLICATIONS

Papadimitriou CG et al. Identification of peptides in traditional and probiotic sheep milk yoghurt with angiotensin I-converting enzyme (ACE)-inhibitory activity. Food Chemistry. 2007; 105(2): 647-656.
Kitazawa et al. Enzymatic digestion of the milk protein beta-casein releases potent chemotactic peptide(s) for monocytes and macrophages. International Immunopharmacology. 2007; 7(9): 1150-1159.
Jinsmaa et al. Enzymatic release of neocasomorphin and beta-casomorphin from bovine beta-casein. Peptides, 1999; 20(8): 957-962.
Carey et al, The effect of probiotics and organic acids on Shiga-toxin 2 gene expression in enterohemorrhagic *Escherichia coli* O157:H7. Journal of Microbiological Methods. 2008; 73: 125-132.
Cadieux et al. "Lactobacillus Strains and Vaginal Ecology" JAMA, 287(15):1940-1941 (2002).
Choi et al. "Antiviral Activity of Yogurt against Enterovirus 71 In Vero Cells" Food. Sci. Biotechnol., 19(2):289-295 (2010).
Medellin-Pena et al. "Effect of Molecules Secreted by Lactobacillus acidophilus Strain La-5 on *Escherichia coli* O157:H7 Colonization" Applied and Environmental Microbiology, 75(4):1165-1172 (2009).
Rao et al. "Toward a live microbial microbicide for HIV: Commensal bacteria secreting an HIV fusion inhibitor peptide" Proc. Natl. Acad. Sci., 102(34):11993-11998 (2005).
Torres et al. "Safety, formulation, and in vitro antiviral activity of the antimicrobial peptide subtilosin against herpes simplex virus type 1" Probiotics Antimicrob Proteins, 5(1):26-35 (2013).
Notification of Transmittal of the International Search Report and the Written Opinion of the International Searching Authority, corresponding to International Application No. PCT/CA2014/000618 dated Nov. 12, 2014.
Botic et al. "A novel eukaryotic cell culture model to study antiviral activity of potential probiotic bacteria" International Journal of Food Microbiology, 115:227-234 (2007).

PROBIOTIC BACTERIAL MOLECULES AND THEIR USE IN METHODS TO TREAT/PREVENT INFECTION BY HARMFUL BACTERIA AND TO PROVIDE NUTRITIONAL HEALTH

PRIORITY STATEMENT

This application is a continuation application of U.S. application Ser. No. 13/001,328, filed Mar. 28, 2011, which is a 35 U.S.C. § 371 national phase application of International Application Serial No. PCT/CA2009/00901, filed Jun. 26, 2009, which claims the benefit, under 35 U.S.C. § 119 (a) of U.S. Provisional Patent Application No. 61/076,581, filed Jun. 27, 2008, the entire contents of each of which are incorporated by reference herein.

FIELD OF THE INVENTION

This invention relates generally to the control of pathogenic bacteria in mammals. More particularly, the invention relates to the isolation and identification of molecules secreted/derived from probiotic bacteria for use in compositions and methods for the treatment and/or prevention of infection by harmful pathogenic bacteria. The isolated molecules are useful in nutritional and medical food products which provide probiotics to the gastrointestinal tract of a mammal.

BACKGROUND OF THE INVENTION

Enterohaemorrhagic *Escherichia coli* O157:H7 (EHEC O157) is a member of the attaching and effacing *Escherichia coli* (AEEC) (3) that form specific structures known as attaching and effacing (AE) lesions in the host intestinal epithelial wall, which allow EHEC O157 to intimately attach to the epithelial membrane in order to achieve colonization (18, 22, 24). In AE lesion formation initial attachment of the bacterium is followed by the injection of bacterial proteins into the host cell (8, 17, 21) through a specialized translocation apparatus, termed a type III secretion system (TTSS). This results in the cytoskeletal rearrangement and effacement of the microvilli. Finally a 94-kDa bacterial outer membrane protein, termed intimin is required (19), resulting in the formation of the bacterium-host cell pedestal structure (9, 10, 27, 37).

A number of enteric bacteria, including EHEC, are known to produce and/or respond to chemical signals called autoinducers. The use of this cell-to-cell signaling mechanism facilitates enteric microbes to regulate important traits that allow them to successfully colonize and/or start infection in their host (20). EHEC virulence-specific genes are regulated by quorum sensing (QS) (34, 35) mediated by the autoinducer-3/epinephrine/norepinephrine signaling system (36). Autoinducer-3 (AI-3) is a molecule produced by the commensal gastrointestinal microbiota that seems to resemble the hormones epinephrine and norepinephrine produced by the host (36) and is believed to allow the enteric pathogens to organize a concerted activation/repression of specifically required genes. Furthermore, an EHEC sensor kinase, QseC, which binds AI-3 and the hormones epinephrine/norepinephrine and regulates virulence in a rabbit infection model provides evidence that this QS system participates in interkingdom cross-communication (5). Thus, enteric pathogens possess an extremely complex regulatory system that is used to systematically compete in such a challenging environment and inhibition of this QS system may lead to an attenuation of virulence.

*Salmonella* spp. are widespread with in the environment. *S. typhimurium* DT104 typically is resistant to the antibiotics ampicillin, chloramphenicol, streptomycin, sulphonamides and tetracycline (R-type ACSSuT) (48). *Salmonella enterica* serovar *typhimurium* requires the expression of the TTSS for a number of important virulence factors like bacterial invasion, macrophage apoptosis and enteropathogenesis (41, 43, 44, 46 and 47). TTSS gene transcription is activated in response to environmental signals (39, 40 and 45). Cattle are thought to be a primary reservoir through which *Salmonella* multi-resistant pathogens can enter the food supply.

The human gastrointestinal tract harbors a complex microbial ecosystem containing a large number and variety of bacteria that has a major impact on gastrointestinal function and thereby on human health and well-being. Among these, some opportunistic bacteria are considered to be detrimental and cause adverse conditions such as diarrhea, infections, gastroenteritis and endotoxaemia, while other bacteria are considered "probiotic", in that they perform beneficial functions for the human organism (49).

Probiotic bacteria are known to stimulate the immune system and exert a competitive exclusion of pathogenic and putrefactive bacteria, reduce the amounts of ammonia and cholesterol in the blood, and promote absorption of minerals (50). Additionally, probiotic bacteria produce antagonist effects against pathogenic microorganisms; stimulate the immune system; improve lactose digestion; are lipolytic, thereby allowing fats to be more digestible; reduce plasma cholesterol; protect the intestinal mucosa, thereby assuring effective assimilation of the nutritive substances; produce polysaccharides that are active on some tumors; and reduce viability of some enzyme-producing microorganisms which catalyze the conversion of procarcinogenic substances into carcinogenic substances. It is believed that the probiotic bacteria exert their effects in a synergistic manner to curtail and retard the growth of pathogenic and detrimental bacteria of the gut (51 and 52).

It is believed that the health and well being of people and animals can be positively or negatively influenced by the microorganisms which inhabit the gastrointestinal tract, and in particular the large bowel. These microorganisms through the production of toxins, metabolic by-products, short chain fatty acids, and the like affect the physiological condition of the host and improve the physiological well being of the host. As a result, research has focused on using probiotic cultures in a variety of compositions and methods to improve health.

For example, US 20040161422 discloses a nutritional food product comprising at least one probiotic bacteria to improve gut function. U.S. 20040115177 discloses methods of administering probiotic bacteria to livestock animals in an amount effective to reduce the amount of hazardous bacteria. Dietary supplements such as those for example sold as part of the PARINAT™ line is formulated with *Lactobacillus acidophilus* strain L.B. and is stated to be beneficial for general digestive and intestinal problems.

Studies have also determined that *L. acidophilus* La-5 may affect virulence-related gene expression in *Escherichia coli* O157:H7 (29). La-5 cell spent medium was used and found to affect bacterial transcriptional regulators, however, the studies were all conducted in vitro or *Escherichia coli* cultures and thus the conclusions could not support or identify the bacterial factor(s) responsible for the regulation of the EHEC O157 QS system. It was thus concluded in the study that animal models were required to characterize the efficacy and potential use of the *L. acidophilus* La-5 in mammalian therapeutic embodiments.

In view of the foregoing, it would be desirous to isolate and characterize the factor(s) produced by probiotic bacteria that provide beneficial effects in mammals for prophylaxis, prevention and treatment of harmful bacterial infection as well as use of such molecules as nutritional and food supplements for general health.

SUMMARY OF THE INVENTION

The invention provides novel molecules secreted/derived from probiotic bacteria. The novel molecules are secreted/derived from probiotic bacteria meaning that they are secreted by probiotic bacteria directly into the medium or derived from culture fractions.

The invention thus provides isolated probiotic proteinaceous fractions from probiotic bacteria and also provides the novel molecules from isolated from such fractions. The invention describes the isolation, characterization and methods of use of the molecules of the invention to prevent or treat infection by harmful bacteria as an alternative or adjunct to traditional antibiotic therapy. The molecules of the invention can be used ingested to improve health and incorporated into beverage and food sources to improve nutritional qualities.

The molecules of the invention are low molecular weight and in aspects, proteinaceous as well as heat-stable and partially affected by enzymatic treatment. The secreted molecules of the present invention can also be used as a nutritional supplement to help maintain and/or increase the general health of a mammal and may be incorporated into a variety of food and beverage products for ease of ingestion as well as incorporated into medicaments. As such the secreted molecules of the present invention can be regarded in one aspect as probiotic. By "probiotic" it is generally defined as a live microbial food supplement which beneficially affects the host human or animal by improving its intestinal microbial balance. However, in the present invention "probiotic" is meant to encompass the secreted molecules from probiotic bacteria.

According to an aspect of the present invention are isolated secreted molecules from probiotic bacteria, said secreted molecules being effective in vitro and in vivo to prevent and/or treat bacterial infection.

According to an aspect of the present invention are isolated secreted molecules from probiotic bacteria, said secreted molecules being effective for mammalian nutritional health.

According to another aspect of the present invention are compositions comprising lyophilized probiotic proteinaceous fractions as effective in the prevention and/or treatment of infection by harmful bacteria. Such lyophillized fractions may also be used as a source of mammalian nutritional health.

According to another aspect of the present invention are isolated secreted molecules from a probiotic bacteria selected from *Lactobacillus*, *Bifidobacteria* and *Streptococcus*. In aspects, the *bifidobacteria* is a species selected from *Bifidobacterium longum*, *Bifidobacterium bifidum*, *Bifidobacterium infantis Bifidobacterium crudilactis*. In other aspects, the probiotic bacteria is a *Lactobacillus* selected from *Lactobacillus acidophilus* (La-5), *Lactobacillus fermentum*, *Lactobacillus rhamnosus*. In other aspects the bacterium is *Lactococcus Lactis*. Still in other aspects the probiotic bacteria is from a *Streptococcus* such as *Streptococcus thermophilus*.

According to another aspect of the invention, the secreted molecules of the present invention are effective for treatment and prophylactic therapy against infectious bacteria such as but not limited to EHEC O157:H7 and *Salmonella enterica*.

According to another aspect of the invention is a composition comprising one or more secreted molecules from a probiotic bacterium, said composition being effective to reduce and/or prevent harmful bacterial infection in mammals.

According to another aspect of the invention is a composition comprising one or more secreted molecules from a probiotic bacterium and an antibiotic, said composition being effective to reduce and/or prevent harmful bacterial infection in mammals.

According to another aspect of the invention is a composition comprising one or more secreted molecules from a probiotic bacterium, a sugar source and optionally an antibiotic, said composition being effective to reduce and/or prevent harmful bacterial infection in mammals. In aspects, the sugar source comprises glucose.

According to another aspect of the invention is a composition comprising one or more secreted molecules from a bacteria selected from *Lactobacillus*, *Bifidobacterium* and *Streptococcus* and mixtures thereof.

In aspects of the invention, the secreted molecules are proteinaceous. In further aspects of the invention, the secreted molecules are small, low molecular weight peptides. In further aspects, the secreted molecules can withstand heating at up to about 90° C., freezing, thawing, lyophilization and/or spray drying.

According to another aspect of the invention is a secreted molecule from *Lactobacillus acidophilus* (La-5), wherein said molecule comprises one of the following sequences: YPVEPF, YPPGGP, YPPG and NQPY.

According to another aspect of the invention is a composition comprising a secreted molecule from *Lactobacillus acidophilus* (La-5), wherein said molecule can inhibit colonization by EHEC O157:H7 in vivo in a mammal.

According to another aspect of the invention is a composition comprising a secreted molecule from *Lactobacillus acidophilus* (La-5), wherein said molecule comprises one of the following amino acid sequences: YPVEPF, YPPGGP, YPPG and NQPY and said molecule can prevent and/or treat infection of EHEC O157:H7. The amino acid sequences may have substitutions that do not adversely affect the activity of the secreted molecule.

According to another aspect of the invention is a composition comprising a secreted molecule from a *Bifidobacterium* selected from *Bifidobacterium longum*, *Bifidobacterium bifidum* and *Bifidobacterium infantis* and/or *Bifidobacterium crudilactis*, wherein said composition can prevent and/or treat infection of EHEC O157:H7 in viva in a mammal.

According to another aspect of the invention is a food product, beverage product, medicament or nutritional supplement that comprises one or more secreted molecules of the present invention from a bacterium selected from *Lactobacillus acidophilus* (La-5), *Lactobacillus fermentum*, *Lactobacillus rhamnosus*, *Lactococcus Lactis*, *Streptococcus thermophilus*, *Bifidobacterium longum*, *Bifidobacterium bifidum*, *Bifidobacterium infantis*, *Bifidobacterium crudilactis*, *Streptococcus thermophilus* and combinations thereof.

According to another aspect of the invention is an ingestible health product for mammals, wherein said ingestible health product has probiotic characteristics and comprises one or more secreted molecules from *Lactobacillus acidophilus* (La-5), *Lactobacillus fermentum, Lactobacillus rhamnosus, Lactococcus Lactis, Streptococcus thermophilus, Bifidobacterium longum, Bifidobacterium bifidum* and *Bifidobacterium infantis* and/or *Bifidobacterium crudilactis*.

According to another aspect of the present invention is a method for preventing and/or therapeutically treating infections by *Escherichia coli* O157:H7 and/or *Salmonela*, the method comprising administering to a subject an effective amount of a composition comprising one or more secreted molecules from *Lactobacillus acidophilus* (La-5). In aspects, the secreted molecules may further comprise those from *Lactobacillus fermentum, Lactobacillus rhamnosus, Lactococcus Lactis, Streptococcus thermophilus, Bifidobacterium longum, Bifidobacterium bifidum, Bifidobacterium infantis, Bifidobacterium crudilactis, Streptococcus thermophilus* and combinations thereof.

The present invention also provides a method for preventing the carriage by a food production animal of *Salmonella* strains that cause human salmonellosis. The method comprises the step of administering an effective amount of secreted molecules from probiotic bacteria to the food production animal prior to exposure to *Salmonella* strains that cause human salmonellosis. The administration of the secreted molecules from probiotic bacteria is accomplished by feeding a feed supplement or additive which comprises an effective amount of said secreted molecules, or by supplying a water treatment additive or inoculum to the animals' drinking water. The invention therefore provides a feed supplement composition comprising secreted molecules from probiotic bacteria and a water additive comprising secreted molecules from probiotic bacteria. The probiotic bacteria may be selected from the group consisting of *Lactobacillus acidophilus* (La-5), *Lactobacillus fermentum, Lactobacillus rhamnosus, Lactococcus Lactis, Streptococcus thermophilus, Bifidobacterium longum, Bifidobacterium bifidum, Bifidobacterium infantis, Bifidobacterium crudilactis, Streptococcus thermophilus* and combinations thereof.

According to another aspect of the present invention is a method of preventing infection by harmful bacteria in a mammal, the method comprising administration of an effective amount of a secreted molecule(s) from a probiotic bacteria selected from the group consisting of *Lactobacillus acidophilus* (La-5), *Lactobacillus fermentum, Lactobacillus rhamnosus, Lactococcus Lactis, Streptococcus thermophilus, Bifidobacterium longum, Bifidobacterium bifidum, Bifidobacterium infantis, Bifidobacterium crudilactis, Streptococcus thermophilus* and combinations thereof.

According to another aspect of the present invention is a method of preventing colonization by harmful bacteria in a mammal, the method comprising administration of an effective amount of a secreted molecule(s) from a probiotic bacteria selected from the group consisting of *Lactobacillus acidophilus* (Lo-5), *Lactobacillus fermentum, Lactobacillus rhamnosus, Lactococcus Lactis, Streptococcus thermophilus, Bifidobacterium longum, Bifidobacterium bifidum* and *Bifidobacterium infantis* and/or *Bifidobacterium crudilactis*.

According to another aspect of the present invention is a method of improving the general health of a mammal, the method comprising administration of an effective amount of a secreted molecule(s) from a probiotic bacteria selected from the group consisting of *Lactobacillus acidophilus* (La-5), *Lactobacillus fermentum, Lactobacillus rhamnosus, Lactococcus Lactis, Streptococcus thermophilus, Bifidoboc-teriurn longum, Bifidobacterium bifidum* and *Bifidobacterium infantis* and/or *Bifidobacterium crudilactis*.

In any of the aforementioned methods of the invention, the molecule(s) of the invention may be provided isolated and/or purified or within a cell free culture fraction from the probiotic bacteria. Alternatively, the secreted molecules may be provided within a composition, edible food product or supplement or ingestible liquid. They can be used in conjunction with whole probiotic bacteria and with pharmaceuticals such as known antibiotics.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE EMBODIMENTS

Figure 1:
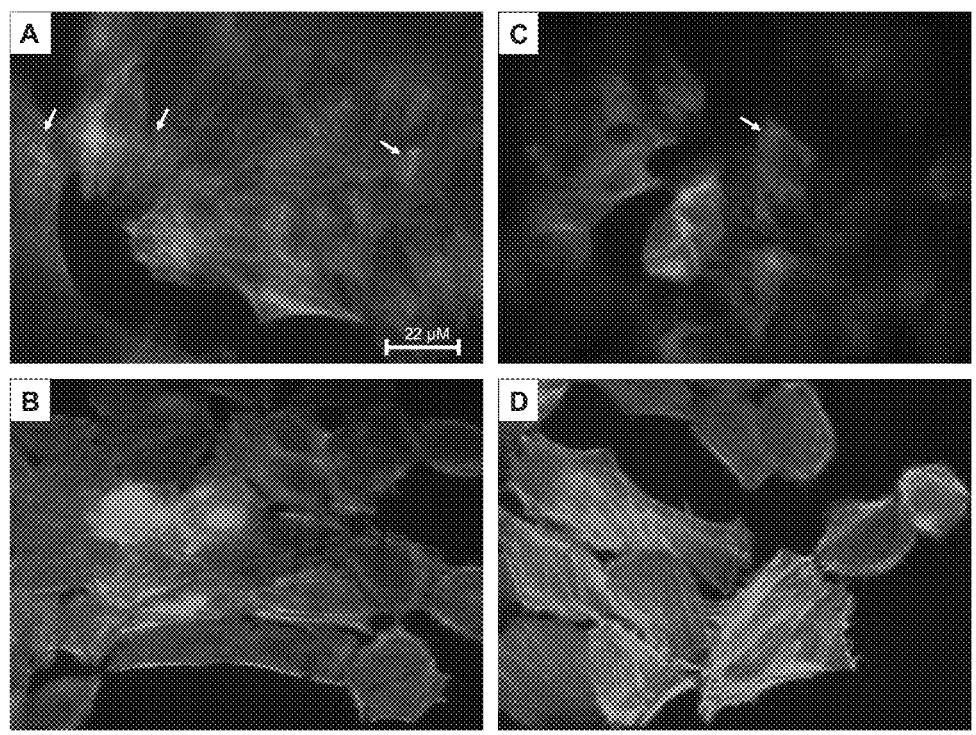
FIG. 1. Fluorescent micrographs of HEp-2 cells incubated for 6 h with EHEC strain 43984. Bright fluorescence with the fluorescein isothiocyanate-phalloidin stain, indicating aggregation of foci of alpha-actinin underneath adherent EHEC (arrows) was visualized under the microcolonies by fluorescence microscopy. (A) Infected cells; (B) Non-infected cells; (C) EHEC infected cells co-incubated with 40 μl of peptide fraction of *L. acidophilus* La5; and (D) EHEC LuxS (-ve) infected cells. Original magnification, 40×. Bar, 22 μm. Images are representative of three independent assays.

The present invention provides secreted molecules isolated from probiotic bacteria and further culture fractions of the bacteria that can minimize, inhibit and treat infection by harmful enteric pathogens in mammals. The molecules are demonstrated to be effective both in vitro and in vivo. In particular, the molecule(s) have been isolated and characterized from *Lactobacillus acidophilus* (La-5) as well as from strains of *Bifidobacterium* such as but not limited to *Bifidobacterium longum*, *Bifidobacterium bifidum*, *Bifidobacterium infantis* and *Bifidobacterium crudilactis* (Delcenserie, V., F. Gavini, H. Beerens, O. Tresse, C. Franssen, and G. Daube. 2007. Description of a new species, *Bifidobacterium crudilactis* sp. nov., isolated from raw milk and raw milk cheeses. Syst Appl Microbiol. 30:381-9: Daube, G., V. Delcenserie, and F. Gavini. 31-03-2006, 2006. Probiotic *Bifidobacterial* Species. International Patent Application: PCT/EP2006/061247, the contents of which are all incorporated herein by reference) and also from *Lactobacillus fermentum*, *Lactobacillus rhamnosus*, *Loctococcus Lactis* and *Streptococcus thermophilus*. The secreted molecules are now shown effective against colonization of *Escherichia coli* O157:H7 and *Salmonella*.

By 'secreted/derived' is meant that the probiotic bacteria secrete the novel molecules directly into the culture medium. In aspects, the molecules can also be formed indirectly within the culture medium.

The novel secreted molecules of the invention in aspects are small peptides that are temperature resistant (can be heated, frozen and thawed and still exhibit activity), are stable for long periods of time frozen (over two years), can be produced readily in large volumes (for example about 2 mg/L), can be lyophilized and spray dried. The molecules can be incorporated into a variety of substances for administration to a mammal such as any type of animal and humans. For example, the secreted molecules car be incorporated into any type of food product, nutritional supplement or beverage for animal or human consumption. As a therapeutic, the secreted molecules of the invention can be administered in a manner to an animal or human for the effective treatment of bacterial infection such as by EHEC O157:H7 or *Salmonella*. As a therapeutic or prophylactic, the treatment can be in conjunction with other antibiotics or other therapies as is desired. In another embodiment, the secreted molecules of the invention can be used in compositions and in methods in addition to use of whole probiotic bacteria.

In aspects the secreted molecules are isolated from *Lactobacillus acidophilus* (La-5), wherein said molecule comprises one or more of the following amino acid sequences: YPVEPF, YPPGGP, YPPG and NQPY. It is understood by one of skill in the art that these sequences can be altered by deletion, substitution or insertion so long as the activity of the secreted molecules is not substantially affected to reduce and/or prevent bacterial infection.

The sequences can further have insertions, substitutions, or deletions of one or more of the amino acid residues. Furthermore, the molecules of the invention may further be altered with glycosylation, unglycosylation, organic and inorganic salts and covalently modified. Also encompassed are molecules modified to increase in vivo half life, e.g., PEGylated. Possible but non limiting modifications to the molecules of the invention include modifications comprising combinations of amino acid substitutions together with a deletion of one or more amino acids or the addition of one or more amino acids.

In a generalized aspect of the invention, the molecules of the invention can be provided in a therapeutically effective amount alone or within a composition and may vary according to factors such as the infection state/health, age, sex, and weight of the recipient. Dosage regima may be adjusted to provide the optimum therapeutic response and may be at the discretion of the attending physician or veterinarian. For example, several divided doses may be administered daily or on at periodic intervals, and/or the dose may be proportionally reduced as indicated by the exigencies of the therapeutic situation. The amount of the molecule for administration will depend on the route of administration, time of administration and varied in accordance with individual subject responses. Suitable administration routes are intramuscular injections, subcutaneous injections, intravenous injections or intraperitoneal injections, oral and intranasal administration. Compositions comprising the molecules or the culture fractions of the invention may comprise about 0.1% to about 90% by weight of the active and any range there-in-between.

The molecules or culture fractions may be administered over a period of hours, days, weeks, or months, depending on several factors, including the severity of the infection being treated, whether a recurrence of the infection is considered likely, or to prevent infection etc. The administration may be constant, e.g., constant infusion over a period of hours, days, weeks, months, etc. Alternatively, the administration may be intermittent, e.g., the molecules may be administered once a day over a period of days, once an hour over a period of hours, or any other such schedule as deemed suitable.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456 (the entirety of which is incorporated herein by reference).

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

For example, in accordance with a veterinary embodiment of the invention, a composition containing the secreted molecules in an acceptable carrier is administered to an animal at least about three weeks prior to shipment of the animal in an amount effective to reduce the amount of *Salmonella* in the animal both before and after harvest. The secreted molecules from probiotic bacteria may be delivered in an acceptable carrier via a food route of administration (e.g., milk product, water, feed, or any suitable medium) or by a medicinal route of administration (e.g., oral or intranasal innoculation). Acceptable carriers for the secreted molecules from probiotic bacteria include feed products for the livestock animal, including, for example, milk or yogurt cultures. A dry form of the secreted molecules from probiotic culture can also be produced and added to feed by the process of lyophilization. Lyophillized secreted molecules may be delivered to animals by any suitable route of administration including via dry feed and water. By administering such therapy in advance of transport, significant levels of hazardous bacteria such as *Salmonella*, are reduced in the livestock pre and post slaughter.

In another non-limiting embodiment of the present invention administration of the isolated secreted molecules from probiotic bacteria can be accomplished by any method likely to introduce the molecules into the digestive tract. The bacteria can be mixed with a carrier and applied to liquid or solid feed or to drinking water. The carrier material should be non-toxic to the animal. The molecules can also be formulated into a composition provided as an inoculant paste to be directly injected into an animal's mouth. The formulation can include added ingredients to improve palatability, improve shelf-life, impart nutritional benefits, and the like. If a reproducible and measured dose is desired, the molecules can be administered by a rumen cannula, as described herein. The amount of the secreted molecules isolated from probiotic bacteria to be administered is governed by factors affecting efficacy. By monitoring the numbers of *E. coli* O157:H7 in feces before, during and after administration of the secreted molecules from probiotic bacteria, those skilled in the art can readily ascertain the dosage level needed to reduce the amount of *E. coli* O157:H7 carried by the animals. The secreted molecules from one or more strains of probiotic bacteria can be administered together. A combination of strains can be advantageous because individual animals may differ as to the strain which is most persistent in a given individual.

The secreted molecules from probiotic bacteria can be administered as a preventive, to prevent animals not presently carrying *E. coli* O257:H7 from acquiring the strain by exposure to other animals or environments where *E. coli* O157:H7 is present. Young calves and mature animals about to be transferred to a new location, such as a feed lot, are attractive candidates for preventive administration, Treatment of animals carrying *E. coli* O157:H7 can be accomplished to reduce or eliminate the amount of *E. coli* O157:H7 carried by the animals, by administering the secreted molecules from probiotic bacteria to *E. coli* O157:H7 infected animals. Animals known to be shedding *E. coli* O157:H7 in feces, or those raised where *E. coli* O257:H7 is known to exist are suitable candidates for treatment with the molecules of the invention.

The methods for administering the secreted molecules from probiotic bacteria are essentially the same, whether for prevention or treatment. Therefore, the need to first determine whether *E. coli* O157:H7 being carried by the animals is removed. By routinely administering an effective dose to all the animals of a herd, the risk of contamination by *E. coli* O157:H7 can be substantially reduced or eliminated by a combination of prevention and treatment.

It is understood by one of skill in the art that the isolated molecules and culture fractions containing such, can be used in conjunction with known antibiotic therapies for prevention and/or treatment of bacterial infection in mammals. It is also understood that compositions of the novel molecules of the invention whether isolated or in isolated culture fraction can also be used in conjunction (formulated with) with a sugar source such as for example glucose in amounts of up to about 0.01% to about 0.1% or more by weight of the composition.

It is also understood that although the compositions of the invention may be directly ingested or used as an additive in conjunction with foods, it will be appreciated that they may be incorporated into a variety of foods and beverages including but not limited to yoghurts, ice creams, cheeses, baked products such as bread, biscuits and cakes, dairy and dairy substitute foods, confectionery products, edible oil compositions, spreads, breakfast cereals, juices and the like. Within the scope of the term "foods" are to be included in particular food likely to be classified as functional foods, i.e. "foods that are similar in appearance to conventional foods and are intended to be consumed as part of a normal diet, but have been modified to physiological roles beyond the provision of simple nutrient. Similarly, the compositions of the invention may be presented in dosage forms such as in a capsule. Again, amounts of the active isolated molecule will vary depending on the particular food or beverage and may contain any amount up to about 100% of the product, especially when formulated as an ingestible capsule. It is also understood by one of skill in the art that the molecules of the invention whether isolated or provided as within a culture fraction can be combined with the use of probiotic bacteria in methods of treatment or for nutritional supplementation.

Lactobacillus acidophilus La-5 CFSM Decreased E. coli O257:H7 Attachment to Tissue Culture Cells.

It was previously demonstrated that L. acidophilus La-5 SM influenced EHEC O157 T3SS (29). Down-regulation of important virulence-related gene expression was presently detected after EHEC O157 was grown in medium supplemented with biologically active fractions of L. acidophilus La-5 CFSM (La-5 fractions) when compared with EHEC O157 grown in the same medium without the addition of La-5 fractions. Presently it was demonstrated that the addition of La-5 fraction would have an influence on EHEC O157 adhesion to eukaryotic cells in vitro and in vivo. Adhesion and AE lesion formation in eukaryotic cells (HEp-2 and HeLa cell lines, respectively) were substantially reduced when La-5 fractions were added before exposure to E. coli O157:H7 strain ATCC 43894. Infection of HeLa cells with EHEC O157 alone showed typical localized adherence behavior (FIG. 1A). However, when it was coincubated with La-5 fraction we could visualize the reduction of actin accumulation underneath attached bacteria (FIG. 1C). HeLa cells infected with EHEC O157 LuxS$^-$ in the presence of propanolol showed no evidence of actin accumulation (FIG. 1D); comparable to non-infected HeLa cells incubated only with the La-5 CFSM selected fraction (F34) (FIG. 1B). To complement the FAS test we performed the adhesion assay with the same EHEC O157 strain 43894 on the HEp-2 cell line. The results of the adhesion assay are summarized in Table 2. Infection of HEp-2 cells with EHEC O157 was normalized to 100% in order to compare with the La-5 treated cells. The degree of attachment was reduced by 76% in the wells containing the La-5 biologically active fraction.

Adherence of EHEC to human epithelial cells involves the activation of the adhesin intimin, an outer membrane protein encoded by the eae gene (9, 26, 27, 37). Previous work (27) showed that production of intimin-specific antisera blocked adherence of EHEC to HEp-2 cells. The immunogenic capacity of intimin has been extensively studied in order to develop anti-EHEC and anti-EPEC vaccines (6, 7, 12, 28). The results demonstrate that secreted molecules from probiotic bacteria could be used to prevent EHEC adherence to epithelial cells in tissue culture models.

Relationship between Infectious Dose of EHEC and Bioluminescent Imaging in ICR Mice.

The optimal infectious dose of EHEC for the bioluminescent imaging of bacterial colonization on SPF ICR mice was determined. Five different cell concentrations, ranging from $10^5$ to $10^9$ cells per dose, were used for a single challenge with EHEC O157 bioluminescent strain. The bioluminescent signal for mice infected with $10^5$ cells was very weak throughout the experiment and only at an inoculation of $10^7$ CFU or greater was the signal strong enough to be visualized and computed (Table 3). Based on previous work in which EHEC O157 proliferated in mice intestines within 24 h of infection (2), it was expected that a dose of $10^5$ CFU would have been enough to emit a strong light output. The aim was to monitor EHEC O157 colonization in vivo in a short period of time, an inoculation dose of $10^8$ CFU was selected for the challenge studies.

L. acidophilus La-5 Biologically Active Fraction Reduces Attachment of EHEC to Intestinal Epithelium of ICR Mice.

Figure 2:
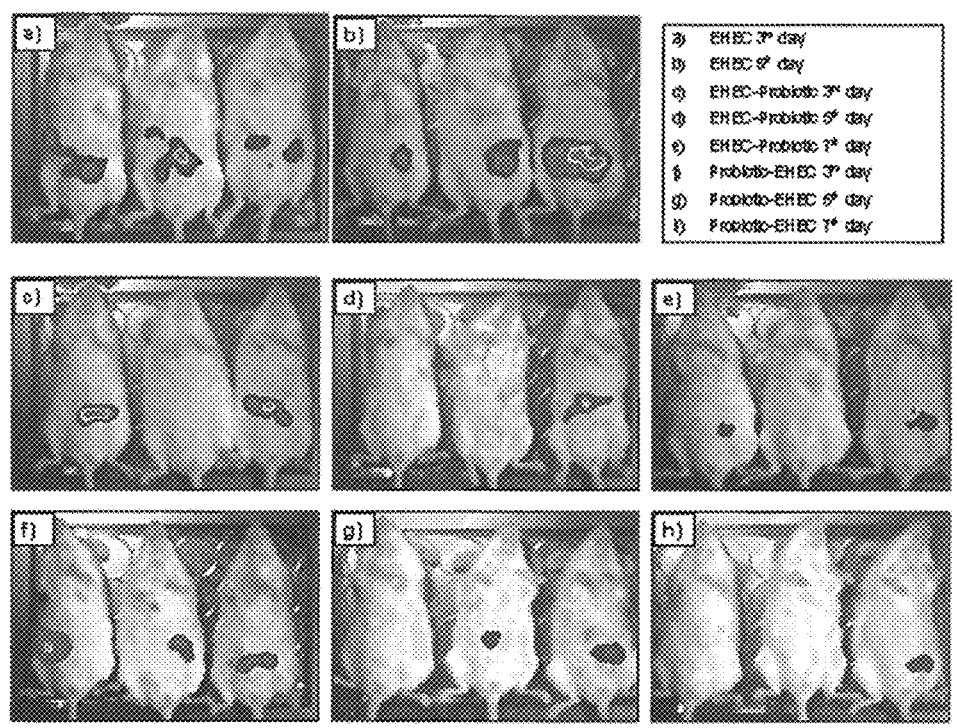
FIG. 2. Bioluminescence images from $10^8$ CFU EHEC O157 infected mice. Images were obtained on the $3^{rd}$, $5^{th}$, and $7^{th}$ day post-infection. Areas in which luminescent EHEC O157 is present are shown as color-overlay.
Figure 3:
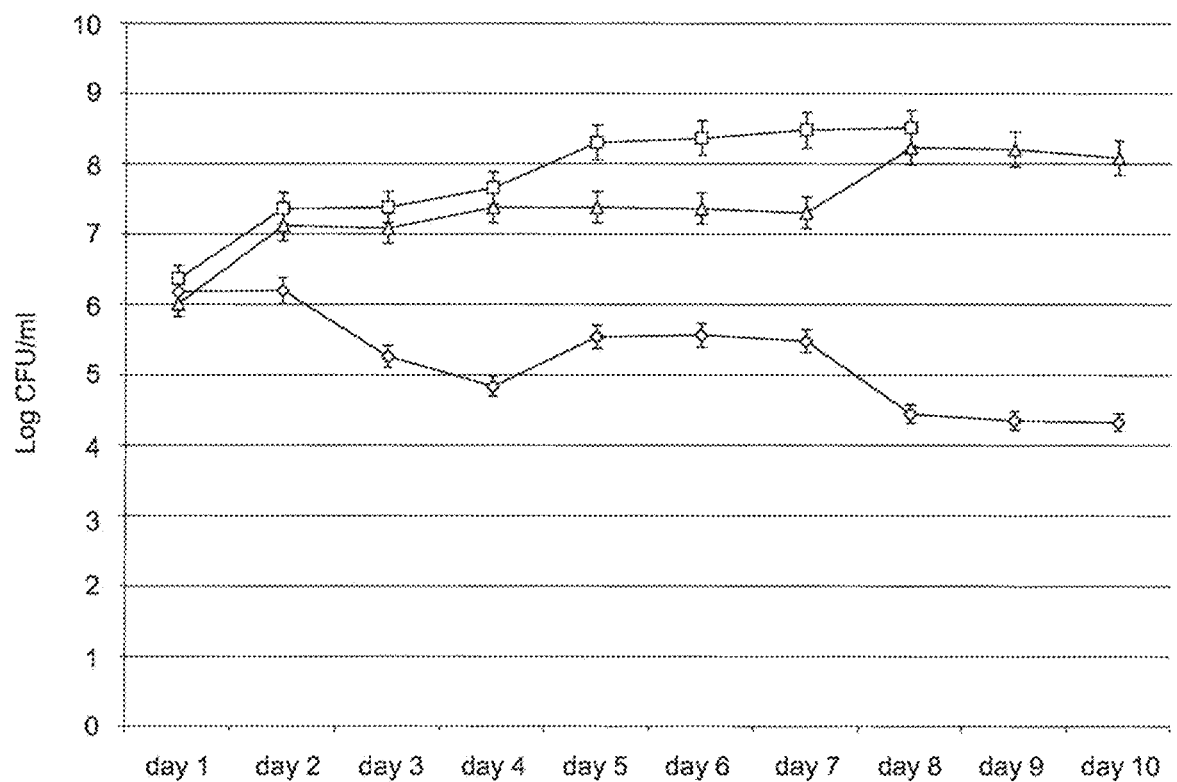
FIG. 3. Average daily fecal shedding of EHEC O157. (◇) group 2 (probiotic-EHEC), (Δ) group 3 (EHEC-probiotic) and (□) group 4 (positive control). The data are average daily fecal values of each group (means±standard deviations, n=5).
Figure 4:
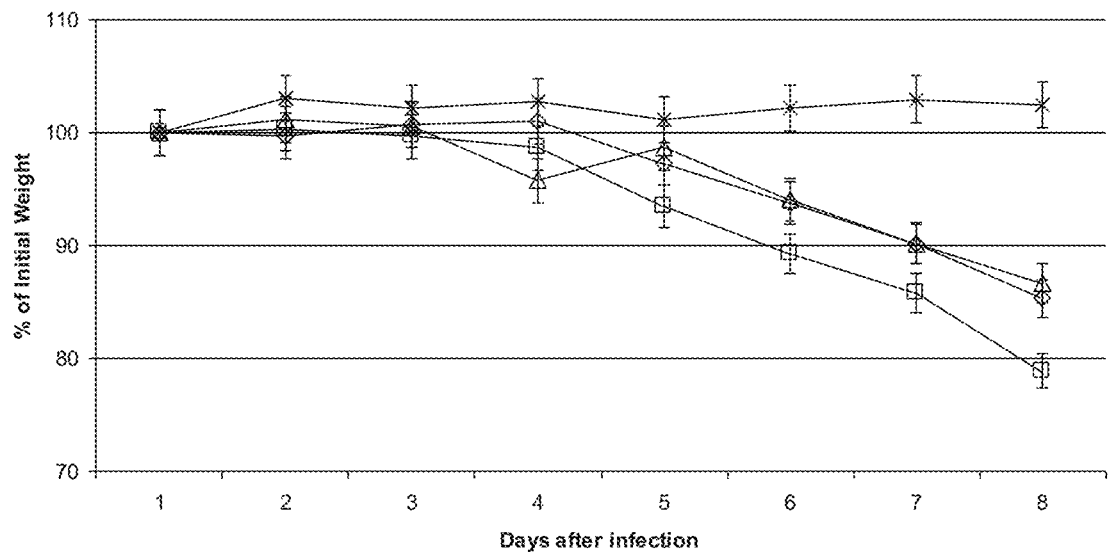
FIG. 4. Body weights of mice during the week following challenge indicated as percentage of initial weights. (x) group 1 (negative control), (◇) group 2 (probiotic-EHEC), (Δ) group 3 (EHEC-probiotic) and (□) group 4 (positive control). The data are average daily weight values of each group (means±standard deviations, n=5).

The ability of EHEC O157 to colonize mice treated with the probiotic La-5 fraction and non-treated ICR mice was compared. EHEC O157 was recovered from the feces of all groups of mice that were infected with the organism (i.e. groups 2, 3 and 4) throughout the study. The proportion of mice shedding EHEC O157 declined significantly over the course of the study in animals that received the La-5 fraction (groups 2 and 3; P=0.0004 and P=0.002, respectively); however, the fecal shedding in mice that were infected with EHEC O157 in the absence of the fraction (group 4) increased to $10^9$ CFU g$^{-1}$ after the fifth day post-infection (FIG. 3). At this time mice from group 4 were showing signs of dehydration and physical deterioration and were re-evaluated every 8 h (FIG. 4), Three mice from group 4 died within the evaluation period and the rest showed a significant reduction in body temperature (<34° C.). At day 5, the end point of group 4 was reached and the remaining mice were euthanized (Table 4). For groups 2 and 3, the condition of the mice remained acceptable ten days post-infection. Bioluminescent signals from mice in groups 2, 3 and 4 were taken and analyzed in order to compare their light intensities at the specified times. On the third day of the experiment, all mice were orally infected with $10^8$ CFU EHEC O157. Bioluminescence was monitored on the third, fifth and seventh day after infection. On the third day after infection, strong bioluminescence was observed in the gastrointestinal (GI) tract of all mice in groups 4 (FIG. 2a) and 3 (FIG. 2c), and two mice from group 2 (FIG. 2f). There was no significant difference in bioluminescence values from all groups of mice at the third day post-infection. However, significant differences were observed after the fifth day post-infection as one mouse from group 2 (FIG. 2g) and two mice from group 3 (FIG. 2d) showed no bioluminescent signal. However, the mouse producing the positive signal from group 3 (FIG. 2d) exhibited strong bioluminescence when compared to the weak bioluminescent signal emanating from the two mice in group 2 (FIG. 2g). Bioluminescence observed at the seventh day post-infection was greatly decreased in both probiotic treated groups indicating that the probiotic La-5 fraction is capable of inhibiting EHEC O157 attachment to intestinal epithelial cells (FIG. 2e and FIG. 2h). It has been proposed that the presence of probiotic bacteria in the host gastrointestinal tract enhances immunity; thereby protecting the host against bacterial infections (11, 13, 31, 32). Taking into account the strain specificity of probiotics (2), employed cell-free spent medium was selected and employed from a probiotic bacterium that down-regulated virulence related genes of EHEC in vitro (29). Due to the ability of probiotic cells to protect animal and human hosts once present in their GI tract (14-16, 30, 33, 38), the present invention focused on the role of probiotic secreted molecules in the control of infection.

Activity Against Other Enteric Pathogens

The effects of secreted molecules of L. acidophilus LA-5 and several strains of bifidobacteria against Salmonella enterica serovar typhimurium virulence gene expression were also demonstrated. The selection of hilA (Hyper Invasive Locus) gene for the gene fusion assay was based on its importance on the gene transcription of the type III secretion system (TTSS) encoded within Salmonella pathogenicity island 1 (SPI1).

Probiotics cell-free spent medium (CFSM) and CFSM fractionated by size exclusion chromatography (SEC) were studied by the LuxS gene fusion assay. LuxS assay was used to determine the expression of hilA (luxCDABE::hilA).

Figure 5:
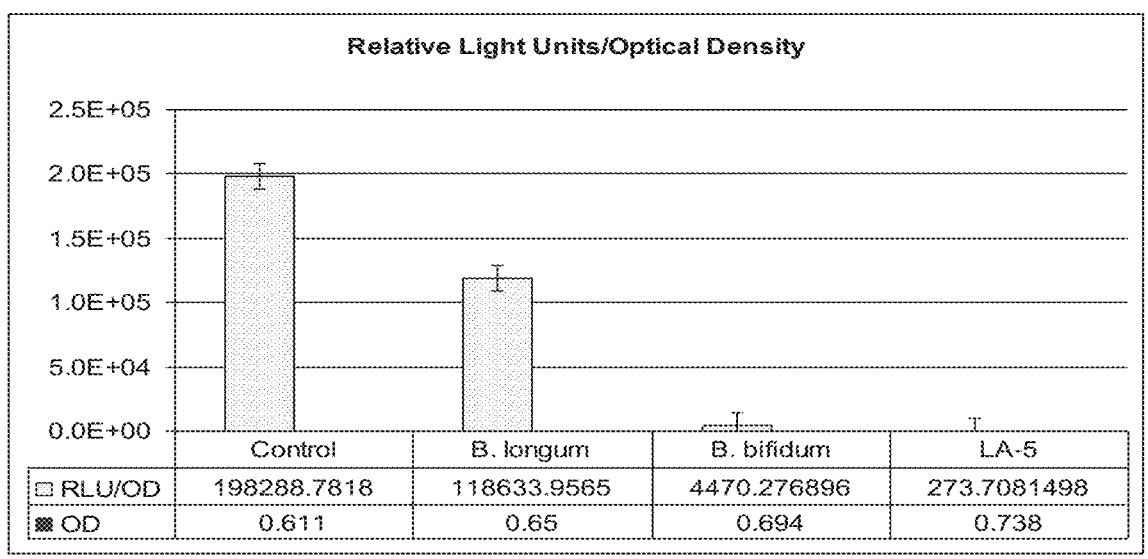
FIG. 5. Effect of LA-5 cell-free spent medium fraction (F54) and *bifidobacteria* CFSM on the induction of hilA in *Salmonella typhimurium* via LuxS assay. Standard deviations from the mean are calculated from 2 independent trials with 3 wells per trial. Expression of hilA gene is monitored by luminescence (RLU) produced by the *Salmonella* construct.

Neither *bifidobacteria* CFSM nor LA-5 CFSM fraction (F54) affected the growth rates of *Salmonella* (FIG. 5). When determined by the LuxS assay, CFSM were found to have an inhibitory effect on the hilA expression compared to the control (FIG. 5).

Activity Produced by Other Probiotic Bacteria

Figure 6:
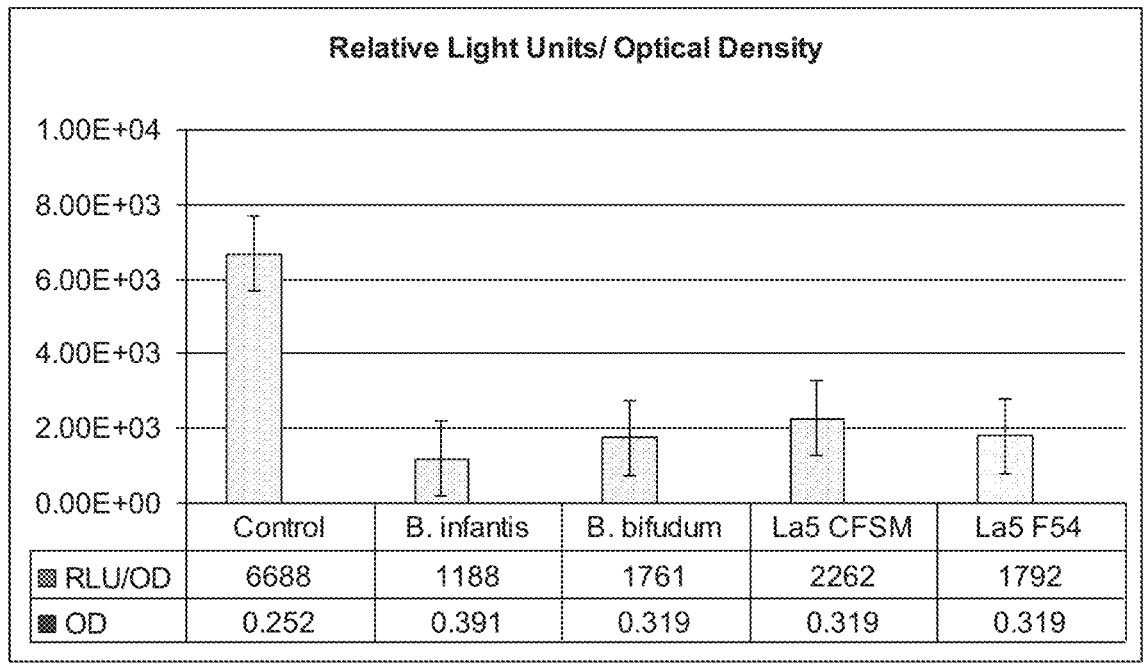
FIG. 6. Effect of LA-5 and *bifidobacteria* CFSM and CFSM fractions (F54) on the induction of LEE1 in Enterohaemorrhagic *E. coli* O157:H7 via LuxS assay. Standard deviations from the mean are calculated from 2 independent trials with 3 wells per trial. Expression of LEE1 is monitored by luminescence (RLU) produced by the *E. coli* O157:H7 construct.

The effects of secreted molecules of several strains of proven probiotic bacteria were also tested: *Bifidobacterium longum*, *Bifidobacterium bifidum*, *Bifidobacterium infantis*, *Bifidobacterium crudilactis* and three *Bifidobacterial* species not yet named against enterohaemorrhagic *Escherichia coli* O157:H7 and *Salmonella enterica* serovar *typhimurium* virulence gene expression via the LuxS assay. Results from these experiments showed that the probiotic strains contain molecules that work in a *L. acidophilus* LA-5-like manner inhibiting induction of LEE1 in enterohaemorrhagic *E. coli* O257:H7 (FIG. 6) and hilA in *S. typhimurium* (FIG. 5). Neither *bifidobacteria* CFSM nor LA-5 CFSM fraction (F54) affected the growth rates of *Salmonella* (FIG. 5) and enterohaemorrhagic *E. coli* O157:H7 (FIG. 6). These preliminary results show differences in inhibitory activity but it is believed due to molecule(s) concentration. All probiotic strains grow at different rates and the protocol used for collecting the bacterial cell-free spent medium was following a 24 h period, since the growth period according to growth rate differences was standardized.

The effect of medium conditioned by the growth of probiotic strains on the expression of virulence-associated genes in *E. coli* O257:1-17 was further characterized as follows to identify further stains of probiotic bacteria effective against EHEC: (1) The activation or repression of LEE operons was monitored using EHEC strain (ATCC 43894) transformed with gene reporter constructs containing luciferase gene luxCDABE (kindly provided by Dr. Haifeng Wang). These constructs operate under the transcriptional control of the LEE promoters. The expression of LEE operons was measured as light emission produced by *E. coli* O257:H7 constructs after exposure to medium conditioned by the growth of the probiotic strains. Probiotic strains used and found effective: *Lactobacillus reuteri* (RC14)(control), *Lactobacillus fermentum* (LFER), *Lactobacillus rhamnosus* (GR1), *Lactococcus lactis* (LL), *Lactobacillus acidophilus* La5 (LA5) and *Streptoccocus thermophilus* (STTH).

Identification of the Active Secreted Molecules

Extracellular fractions from *B. infantis* cultures were studied after 24 h growth. After centrifugation (6000 g, 10 min) of 1 litre of culture, the supernatant was filtered through cellulose acetate membrane filters (pore size: 0.22 µm). The cell-free spent medium (CFSM) was then concentrated via lyophilisation to $\frac{1}{100}$ of the original volume. The lyophilized CFSM was resuspended in molecular Biology grade water and separated by size exclusion chromatography (SEC) and the active fractions were stored at −20° C. for further analysis. Ion exchange chromatography (IEC) was used following the SEC since this is suitable for sample fractionation, purification and screening. The different fractions (basic and acidic proteins concentrated by IEC and their flow-troughs) were then analyzed with the LuxS assay to determine which one of these fractions possesses the desired activity. After we confirm the presence of active molecules the fractions will be used in multidimensional analysis, such as 2-D gel electrophoresis and HPLC. At the same time we will carry out tissue culture assays with *Salmonella enterica* serovar *typhimurium* and possibly other foodborne pathogens.

Figure 7:
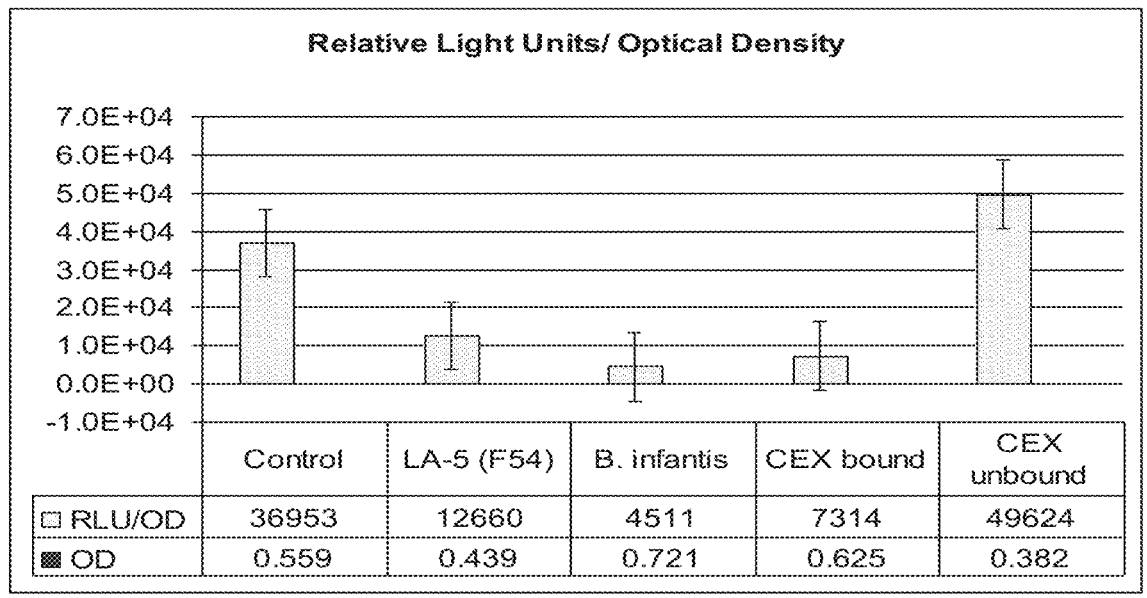
FIG. 7. Effect of LA-5 and *bifidobacteria* CFSM (CFSM fraction 54 [F54] separated by cation exchange chromatography [CEX]) on the induction of LEE1 in Enterohaemorrhagic *E. coli* O157:H7 via LuxS assay. Standard deviations from the mean are calculated from 2 independent trials with 3 wells per trial. Expression of LEE1 is monitored by luminescence (RLU) produced by the *E. coli* O157:H7 construct.
Figure 8:
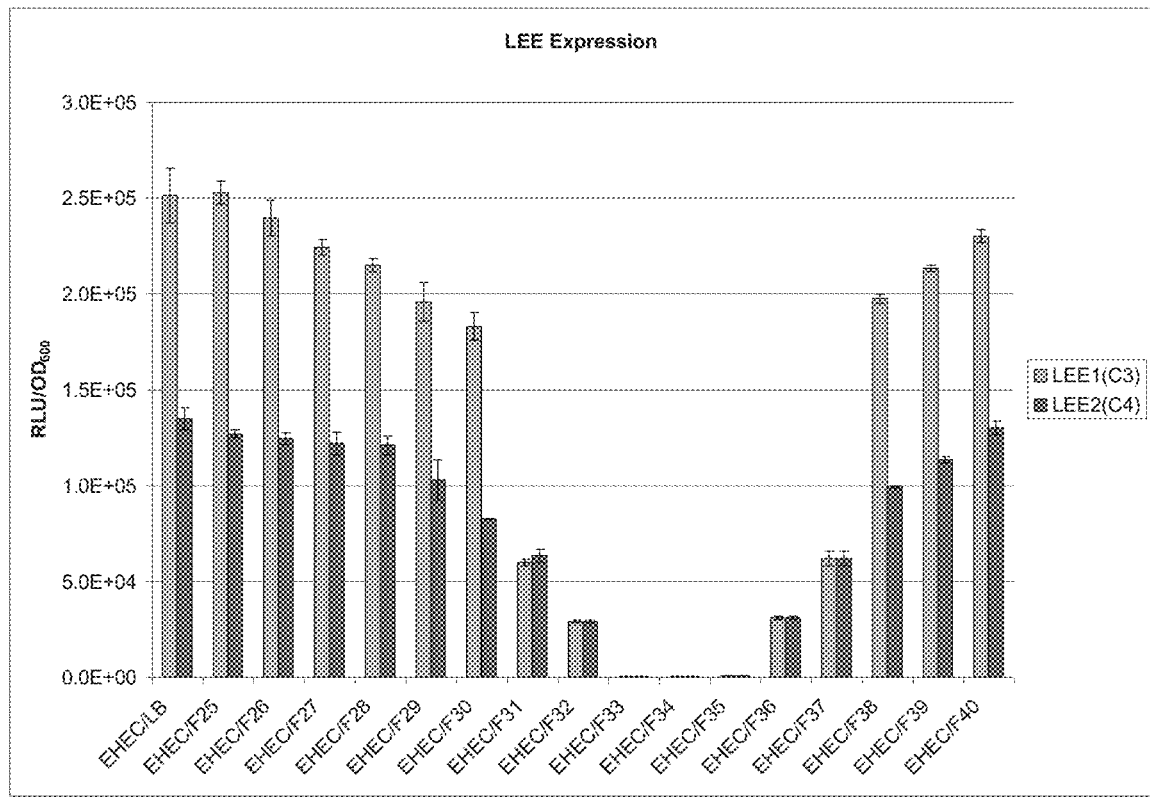
FIG. 8. Luminescence activity of LEE1::luxCDABE and LEE2::luxCDABE fusions in *E. coli* O157:H7 (C3, C4) grown in LB broth alone (EHEC/LB) or in LB broth supplemented with 10% of *L. acidophilus* La-5 CFSM fractions 25 to 40 (EHEC/F). Data was collected after 16 h growth. Results were expressed as relative light units (RLU) defined as counts min$^{-1}$ and adjusted to OD$_{600}$ (RLU/OD$_{600}$). The data are mean±SD values of three independent replicates.
Figure 9:
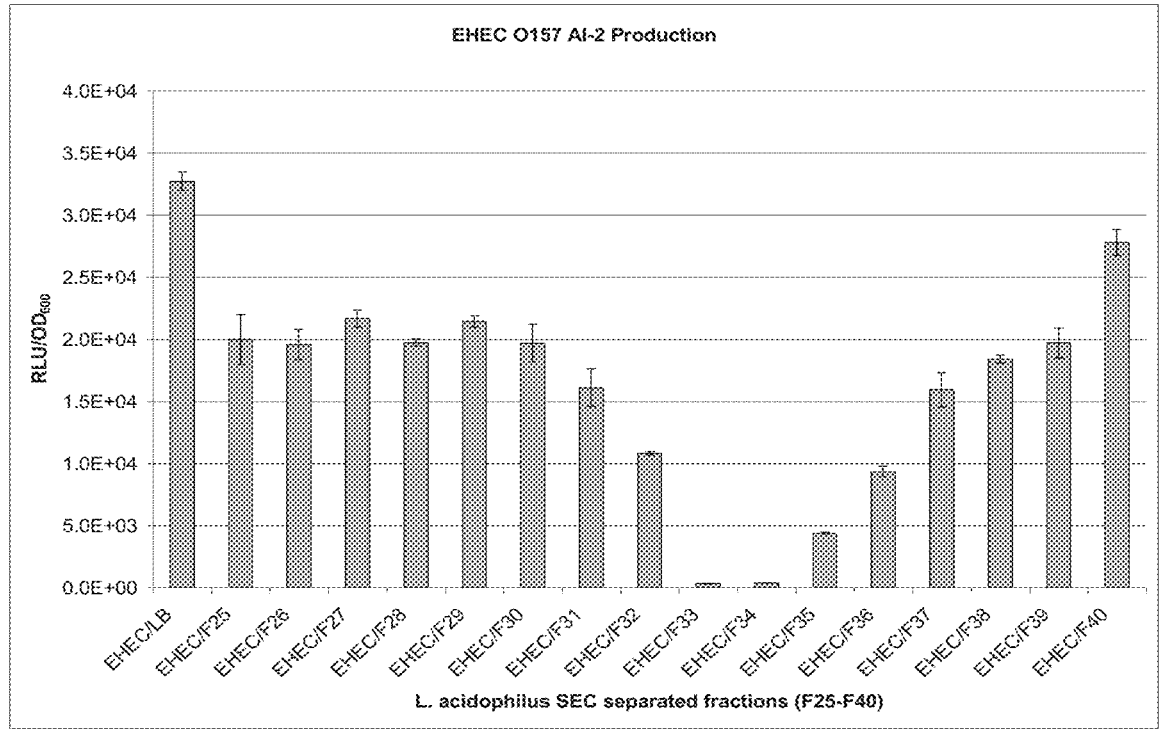
FIG. 9. Autoinducer-2 bioassay conducted three times with the same samples. EHEC O157:H7 (ATCC 43894) was grown for 16 h in LB broth alone (EHEC/LB) or supplemented with 10% of *L. acidophilus* La-5 CFSM fractions 25 to 40 (EHEC/F). The cell-free supernatants from these cultures were collected as described in the methods section. Results were expressed as relative light units (RLU) defined as counts min$^{-1}$ and adjusted to OD$_{600}$ (RLU/OD$_{600}$). The data are mean±SD values of three independent replicates.

Preliminary results show that *B. infantis* CFSM active molecule bound to the cation exchange chromatography column (Aurum CEX, BioRad) suggesting that the molecules may be a small signal peptide possessing basic amino acids residues (FIG. 7).

The first step of separation of molecules from bulk quantities was performed by using size exclusion chromatography (SEC). Following the separated fractions, EHEC O157:H7 bioassays were performed to confirm the presence of the biologically active molecule(s). Consequently, analysis of the biologically active fractions was carried out by electrospray mass spectroscopy (ES-MS) and nuclear magnetic resonance (NMR). Results from the ES-MS and NMR showed that the biologically active fractions were still excessively complex, evading a conclusive report of the nature of the studied fractions. Biologically active fractions were subjected to pH sensitivity, enzymatic and temperature treatments in order to try to shed some light in their nature. Results from these tests, indicated that the biologically active fractions could be very small and of protein nature. Pursuing the necessity for purification, the biologically active fractions were further separated by low-pressure SEC and fractions collected were read at 214 and 280 nm wavelengths and tested again for activity against EHEC O157:H7. Four peaks were collected from which two were still active in vitro. The biologically active fractions consisted of four peptide peaks that were sent for peptide sequencing and the sequences provided herein in the example section.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Cell-Free Fractions

Cell-free fractions were prepared as previously described (25). Briefly, *Lactobacillus acidophilus* strain La-5 was grown overnight in modified DeMann, Rogosa and Sharpe medium. (mMRS; 1.0 g peptone from casein, 8 g meat extract, 4 g yeast extract, 8 g D(+)-glucose, 2 g dipotassium hydrogen phosphate, 2 g di-ammonium hydrogen citrate, 5 g sodium acetate, 0.2 g magnesium sulfate, 0.04 g manganese sulfate in 1. L distilled water) (MRS; BD Diagnostic Systems, Sparks, Md.). The overnight culture was diluted 1:100 in fresh medium. When the culture grew to an optical density at 600 nm ($OD_{600}$) of 1.6 ($1.2 \times 10^8$ cells/ml), the cells were harvested by centrifugation at 6,000×a for 10 min at 4° C. The supernatant was sterilized by filtering through a 0.2-µm-pore-size filter (Millipore, Bioscience Division, Mississauga, ON, Canada) and will be referred to as cell-free spent medium (CFSM). Two litres of *L. acidophilus* La-S CFSM was collected and freeze-dried (Unitop 600 SL, VirTis Co., Inc. Gardiner, N.Y., USA). The freeze-dried CFSM was reconstituted with 200 ml of 18-Ω water. The total protein content of the reconstituted CFSM was quantified using the BioRad DC protein assay kit II (Bio-Rad Laboratories Ltd., Mississauga, ON, Canada). Freeze-dried CFSM was stored at −20° C. prior to the assays.

Example 2

Fractionation of the L. acidophilus La-5 CFSM

Five millilitres of CFSM were directly deposited on a P2 Biogel (Bio-Rad, Missasauga, ON., Canada) column (exclusion, 100 to 1,800 Da; 2.5×100 cm; Bio-Rad Laboratories Ltd.) and run at room temperature in 18-Ω water at a gravity flow rate of 0.8 ml/min, and eighty 5 ml fractions were collected. The fractions collected were freeze-dried and resuspended in 18-Ω water for preliminary screening against EHEC LEE1, LEE2 and AI-2 production as previously described (29). The total protein content of the fractions was quantified using the BioRad DC protein assay kit II. Fractions showing a strong inhibitory activity against LEE expression and AI-2 production were selected.

Example 3

Bacterial Strains

The bacterial strains used in this study are described in Table 1. L. acidophilus strain La-5 was grown under anaerobic conditions at 37° C. in mMRS medium (29). E. coli O157:H7 strain VS94 (36) was grown in Luria-Bertani broth (LB) (BD Diagnostic Systems). The bioluminescent strain of E. coli O157:H7 (luxCDABE) was grown in LB agar supplemented with ampicillin (Amp) and kanamycin (Km) (Sigma-Aldrich Canada Ltd., Oakville, ON, Canada) at a concentration each of 50 µg/ml and incubated overnight at 37° C. A single colony was taken from the plate and subcultured in LB broth and high glucose Dulbecco's minimum essential medium (DMEM/High) (Sigma-Aldrich Canada Ltd.) supplemented with the antibiotics and incubated overnight at 37° C. on a shaker at 150 rpm. The correlation between luminescence and cell count in LB broth was established by a standard plate count technique and by the measurement of the bioluminescence for 1 ml of culture serial dilutions with a tube luminometer (MGM Instruments, Hamden, Conn.), For the infection of the mice, an overnight culture was centrifuged at 13,000×g for 10 min, washed, and resuspended in fresh antibiotic supplemented LB broth.

Example 4

Fluorescent Staining of Actin Filaments

The FAS tests were performed as described previously (23) with some modifications. HeLa, human cervix adenocarcinoma epithelial cells, were provided by Dr. Roger Johnson (Laboratory for Foodborne Zoonoses, Public Health Agency of Canada). HeLa cells were grown in complete Eagle's minimal essential medium (EMEM) (Sigma-Aldrich Canada Ltd.) supplemented with 2% (v/v) fetal bovine serum (FBS) (Invitrogen Canada Inc., Burlington, ON, Canada). Cells were then plated onto 4-well micro-chamber slides at $2\times10^5$ cells $ml^{-1}$ and incubated for 24 h in the presence of 5% $CO_2$. The cells were then maintained during the assay in serum and antibiotic free EMEM. Before inoculation with bacteria, selected fractions of L. acidophilus CFSM (F33 and F34) were added to treatment group wells. As a negative control for AE lesion formation we used an E. coli O157:H7 luxS-negative strain. The negative control group wells were inoculated with $10^5$ E. coli O157:H7 strain VS94 with or without supplementation with 100 µM propanolol, and with only the selected fractions of L. acidophilus. Propanolol was used to suppress complementation of the AE phenotype by the hormones epinephrine and norepinephrine produced by the eukaryotic cells. After inoculation of EHEC O157 strain 43894 into treatment and positive control wells, the slides were incubated for 6 h at 37° C. in the presence of 5% $CO_2$. The cells were then washed three times with phosphate-buffered saline (PBS) and fresh medium was added, Cells were incubated for another 3 h and then washed six times with PBS and fixed in 4% paraformaldehyde. Fixed and washed cells were permeabilized by treating slides with 0.1% Triton X-100 in PBS for 15 min. Cells were incubated with 0.2% bovine serum albumin (BSA) (Invitrogen Canada Inc.) in PBS for 1 h. After three washes in PBS, slides were treated with a 10 µg/ml solution of fluorescein isothiocyanate (FITC) conjugated phalloidin (Sigma-Aldrich Canada Ltd.) in PBS for 40 min to specifically stain actin filaments. Slides were washed three times in PBS and then examined with a Zeiss Axioskope 2 microscope with fluorescence filters for FITC (Carl Zeiss Canada, Inc., North York, ON, Canada). Images were recorded using the Axiocam and Zeiss Axiovision Software (Carl Zeiss Canada, Inc.).

Example 5

HEp-2 Cell Adhesion Assay

In order to compare levels of adherence to HEp-2 epithelial cells in culture, we used an established model for evaluating adherence of EHEC O157:H7 (27). HEp-2, human laryngeal carcinoma epithelial cells, were a kind gift from Dr. Carlton Gyles (Department of Pathobiology, University of Guelph). Briefly, HEp-2 cells grown in EMEM supplemented with 10% (v/v) FBS were plated onto 24-well tissue culture plates at $2\times10^5$ cells $ml^{-1}$ and incubated for 24 h in the presence of 5% $CO_2$. The cells were then maintained during the assay in serum and antibiotic-free EMEM. Before inoculation with bacteria, 10% (v/v) of L. acidophilus CFSM selected fractions were added in triplicate to treatment group wells. Wells containing the negative control groups were inoculated with $10^5$ E. coli O257:H7 strain V594 with or without supplementation with 100 µM propanolol (Sigma-Aldrich Canada Ltd.). Following inoculation of $10^5$ EHEC O157 into treatment and control group wells, the plates were incubated for 3 h at 37° C. in the presence of 5% $CO_2$. The cell monolayers were then washed three times with PBS to remove non-adhering bacteria and fresh medium was added. Cells were incubated for another 3 h and then washed six times with PBS. Washed cells were lysed with 0.1% Triton X-100. Released bacteria present in the suspension were collected and appropriate dilutions were plated on LB agar. To evaluate if the percentage of adherence in the treatment groups was significantly different from that of the control group, where the recovered counts from the control group ($2.2\times10^7$ CFU $m^{-1}$) were considered to be 100%, the percentage of adherence in the negative control and treatment groups were calculated using the following equation.

$$\% \text{ of Recovery} = \frac{\text{Group } CFU \text{ ml}^{-1} \times 100}{2.2\times 10^7}$$

Example 6

Mice Colonization Experiments

SPF female ICR mice were obtained at 3 weeks of age from Taconic Farms (Hudson, N.Y.), and used for the experiments after one-week acclimation. Mice were housed at the Isolation Unit of the Central Animal Facility (University of Guelph) in a temperature controlled environment with a 12 h light/dark cycle. Animal care was provided in accordance with the animal utilization protocol no. 04R030 (University of Guelph) and the *Guide to the Care and Use of Experimental Animals* (1). Mice were fed sterilized solid rodent chow and water. When needed, water was supplemented with Amp and Km at a concentration of 400 mg $L^{-1}$ and 200 mg $L^{-1}$, respectively. Each mouse was assessed daily for weight, body temperature, signs of dehydration, posture and alertness.

Example 7

Mice Experiments

Dose-Response Experiments

Ten mice were divided into 5 equal groups (n=2), and each group was infected by oral gavage with 100 µl of bacterial cell suspension containing $10^5$ to $10^9$ cells. Mice were given the antibiotics required for selection of the luxCDABE-encoding plasmid in their drinking water at concentrations mentioned previously. Sucrose (5% w/v) (Sigma-Aldrich Canada Ltd.) was added in order to make the water supplemented with the antibiotics palatable. The 5% sucrose solution supplemented with the antibiotics was changed daily.

Feeding-Infection Experiments

Mice were divided into four groups. Group 1 was fed with 100 µl of La-5 fraction (negative control) (n=5); groups 2 and 3 were fed daily with 100 µl of La-5 fraction 2 days before (probiotic-EHEC) and 2 days after (EHEC-probiotic) challenge with $10^8$ CFU $ml^{-1}$ EHEC, respectively (n=5); and group 4 (positive control) was infected with $10^8$ CFU $ml^{-1}$ EHEC (n=5). Feeding-infection experiments were repeated three times.

Bioluminescent Imaging

Bioluminescent imaging was performed as previously described (4) with minor modifications. Briefly, bioluminescent imaging was monitored on the $3^{rd}$, $5^{th}$ and $7^{th}$ day after infection. Prior to imaging, mice were anesthetized with a cocktail composed of ketamine (60 mg $kg^{-1}$) and medetomidine (0.75 mg $kg^{-1}$). Atipamezole (2.25 mg $kg^{-1}$) was used to reverse the effects of the anesthetics. All drugs were administered intraperitoneally. Both bioluminescent and photo images of mice were taken with a cooled slow-scan CCD camera (NightOWL Molecular Imager, EG&G Berthold Technologies, Wildbad, Germany). The integration time for bioluminescence was one minute at low resolution. Images were processed with the WinLight software (EG&G Berthold). Pseudocolor images were obtained to represent the distribution of bioluminescent intensity, which changed from blue to yellow to red with increasing light output. Bioluminescent images were superimposed onto photo images of the same mice to locate the origin of bioluminescence. The areas of maximum bioluminescence were identified with the use of the 2D peak search option of the software, and light output from these areas was calculated in terms of relative light unit counts per $cm^2$ per sec (cts $[cm^2 s^{-1}]^{-1}$) with the WinLight program. The dose-response experiment was carried out over 7 days. The feeding-infection experiment was carried out over 12 days or until the end point of the experiment (indicated by a body temperature of <34° C. and/or loss of 20% of body weight) had been reached. At the end point, mice were euthanized with carbon dioxide ($CO_2$).

Enumeration of EHEC O157 Shed in Feces

Fresh feces of mice were weighed and suspended in PBS (0.5 g of feces per 4.5 ml of 0.1% [w/v] sterile peptone water) to obtain a concentration of 100 mg $ml^{-1}$. The fecal suspensions were serially diluted 10-fold and appropriate dilutions were plated in triplicate on LB agar alone and on LB agar supplemented with 50 µg $ml^{-1}$ Amp and Km. Colonies that developed after incubation for 24 h at 37° C. were counted. The limit of detection was $10^2$ CFU $g^{-1}$ feces. A value of $10^2$ $g^{-1}$ feces was assigned to any culture showing no detectable colonies for the purpose of statistical analysis.

Statistical Analysis

All results in this study are means of three independent trials±standard deviations. The Student's t test was used, when necessary, to assess the statistical significance of the differences between test and control groups (P<0.05).

Example 8

Effect of Enzymes, Temperature and pH on CFSM Activity

All active CFSM pH was adjusted to 6.0 with sterile 1N NaOH. Aliquots of the samples were treated with the following enzymes (1 mg $ml^{-1}$) and incubated for 2 h at 30° C.: Proteinase K (Sigma-Aldrich Ltd., Oakville, ON, Canada), trypsin (Sigma-Aldrich) and pepsin (Sigma-Aldrich). The effect of pH on the CFSM was tested by adjusting the CFSM to values ranging from 2.0 to 10.0 (at increments of one pH unit) with sterile 1N NaOH or 1N HCL, and the treated CFSM was incubated for 30 min and 2 h, respectively, at 30° C. The effect of temperature on the activity of the CFSM was tested by heating from 30° C. to 100° C., with increments of 10° C. for a period of 20 min. All treated CFSM were tested for inhibitory activity using the EHEC O157:H7 constructs and the autoinducer bioassay described previously herein.

*L. acidophilus* CFSM and Biologically Active Fractions Total Protein Content.

|  | Total protein content (mg/ml) |
|---|---|
| *Lactobacillus acidophilus* CFSM | 9.7 |
| CFSM pooled fractions | 4.1 |
| Pooled fractions peptide peaks | 2.125 |
| Peak 1 | 1.75 |
| Peak 2 | ND |
| Peak 3 | 0.125 |
| Peak 4 | 0.25 |

ND Protein content not detected

Enzymatic, temperature and pH treatment of the probiotic CFSM. Partial inactivation of inhibitory activity against EHEC O157:H7 LEE expression and AI-2 signaling molecule production was observed after treatment of biologically active CFSM with proteinase K and pepsin (Table 5.2). No reduction in activity was found after treatment with trypsin (Table 5.2). No decrease in activity was recorded after treatment at the different temperatures (30° C., 65° C., 90° C. and 100° C.) for 20 min (Table 5.2). The activity remained after 2 h of incubation at different pH values (2.0, 4.0, 6.0, 7.0 8.0, 9.0 and 10.0) (Table 5.2). None of the CFSM had any antimicrobial activity against EHEC O157:H7, as inhibition of growth was not observed throughout this study. Although most bacteriocins are only active against gram-positive bacteria, we needed to make sure that bacteriocins were not involved in the observed effects. We incubated *L. acidophilus* at a temperature of 37° C. which is known to greatly affect bacteriocin production (Matsusaki et al., 1996). Matzusaki et al. (Matsusaki et al., 1996) demonstrated that the optimal cultivation temperature for the production of nisin Z was 30° C. Together these results eliminate the possibility that the presence of bacteriocins was responsible for the inhibitory effects on the EHEC O157:H7 strains studied Our results demonstrated that the *L. acidophilus* secreted molecules were not affected by changes in culture pH and that the molecule(s) are heat-resistant. The partial inactivation of activity observed after addition of proteinase K and pepsin suggest that they might be small molecules that could consist of short amino acid chains. Nonetheless, these results do not confirm that the active molecules are proteinaceous.

Factors affecting the inhibitory activity of *L. acidophilus* CFSM towards EHEC O157:H7 LEE expression and AI-2 production/uptake.

| Treatment Enzymes (0.1 mg ml$^{-1}$): | Cell-free spent medium activity |
|---|---|
| Proteinase K, pepsin | ± |
| Trypsin | + |
| pH, 2.0-10.0 | + |
| Temperature, 30-100° C. (20 min) | + |

(+) *L. acidophilus* inhibitory activity
(−) No *L. acidophilus* inhibitory activity
(±) 30% *L. acidophilus* inhibitory activity Example 9

Purification of the *L. acidophilus* La-5 Secreted Peptides

Biologically active CFSM fractions were separated by fast pressure liquid chromatography (FPLC) on a Tricorn Superdex 10/300 GL column (Amersham Bioscience, Quebec, Canada) in order to collect and separate the peptides present. The running conditions established by the manufacturer were slightly modified. Briefly, one hundred microliters of CFSM fraction at a protein concentration of approximate 3.5 mg ml$^{-1}$ dissolved in 50 mM sodium phosphate buffer pH 7.0 was injected on the Superdex Peptide column connected to a FPLC pump (ThermoFinnigan A53500, ThermoInstruments Inc., Canada. Missisauga, ON) and eluted with the same buffer at a flow rate of 0.7 ml min$^{-1}$. The absorbance was recorded at 214 and 280 nm by means of a UV detector (SpectraSYSTEM, ThermoFinnigan, ThermoInstruments Inc.). The eluted peaks were pooled, freeze-dried and concentrated 10 times in 18-Ω water. The column was calibrated with α-lactalbumin standard (2.0 mg ml$^{-1}$). The calibration curve was used to determine the average molecular weight of the unknown samples. Chromatographic graphics were obtained using the Chromatography Workstation ChromQuest™. Total protein content of the collected peaks was measured as described previously (Table 5.1). Peptide samples were then desalted and concentrated onto a C$_{18}$ Vivapure® Micro spin columns (Sartorius Biotech Inc., Edgewood, N.Y., USA), and sent to the Biological Mass Spectrometry facility at the University of Guelph (Guelph, ON., Canada) for liquid chromatography-mass spectroscopy (LC-MS) and to the Advance Protein Technology Centre for Edman sequencing at the Hospital for Sick Children (Toronto, Canada).

Figure 10:
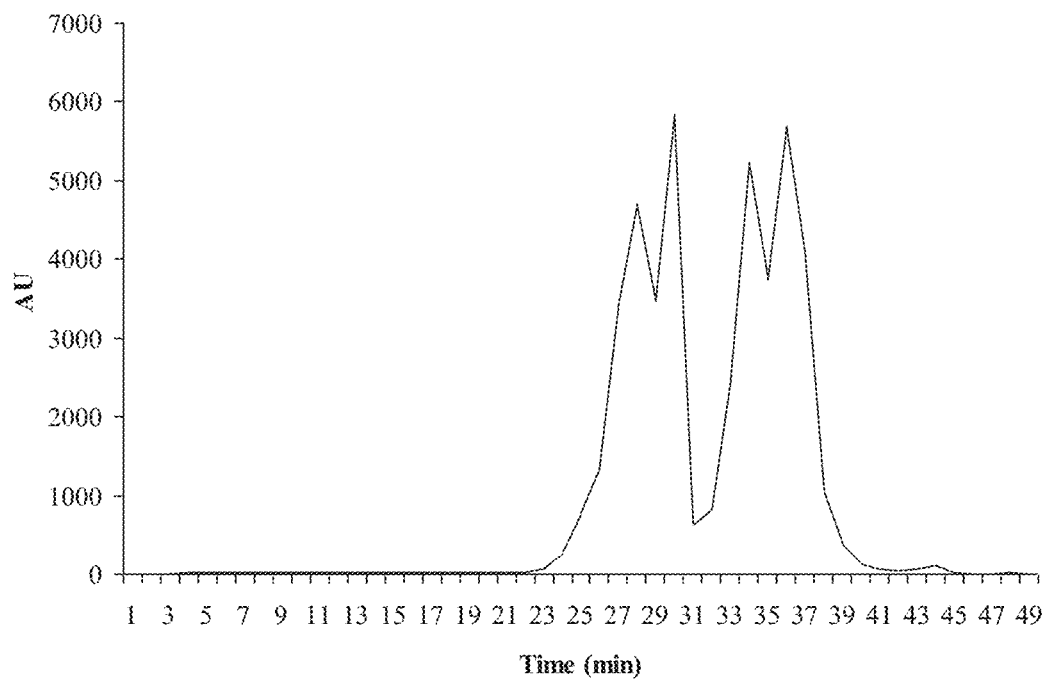
FIG. 10. Fractionation of *L. acidophilus* CFSM peptides by size exclusion FPLC.

Purification of the *L. acidaphilus* La-5 secreted peptides. The FPLC chromatogram results show that the CFSM selected fractions are composed of four peptide fractions (FIG. 10). The molar mass of the peptide fractions was determined to be less than 14,000 Da. α-lactalbumin (MW of 14.2 kDa) was eluted at min 9.3 while the elution of the peptide peaks started at 23 min. These results demonstrate that the fractions contain small peptides that could consist of approximate 2 to 10 amino acid residues.

Figure 11:
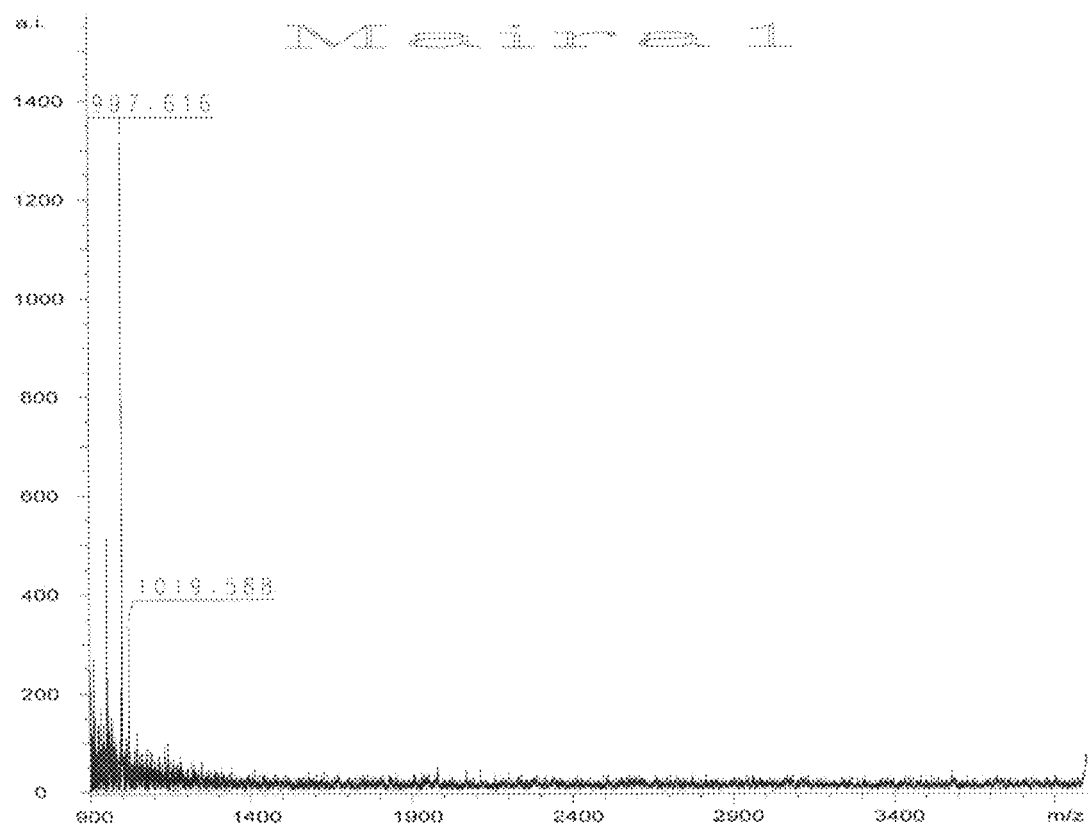
FIG. 11. LC-MS analysis of peptide peak 1 (Maira 1).
Figure 12:
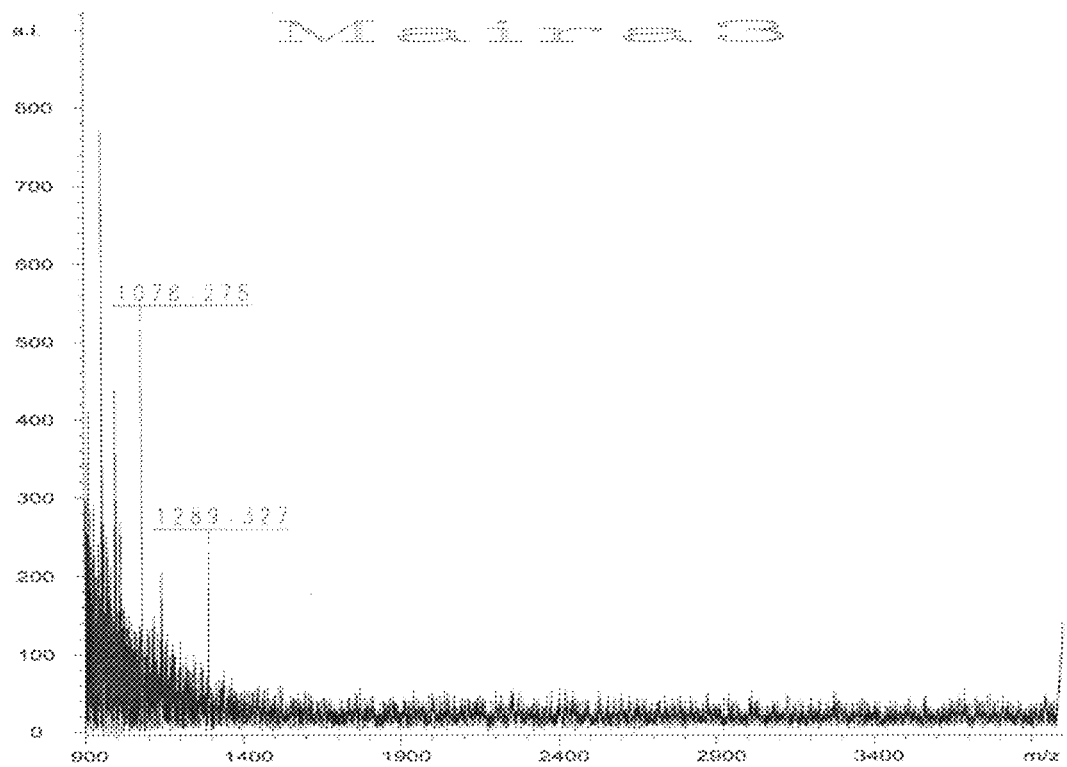
FIG. 12. LC-MS analysis of peptide peak 1 (Maira 3).
Figure 13:
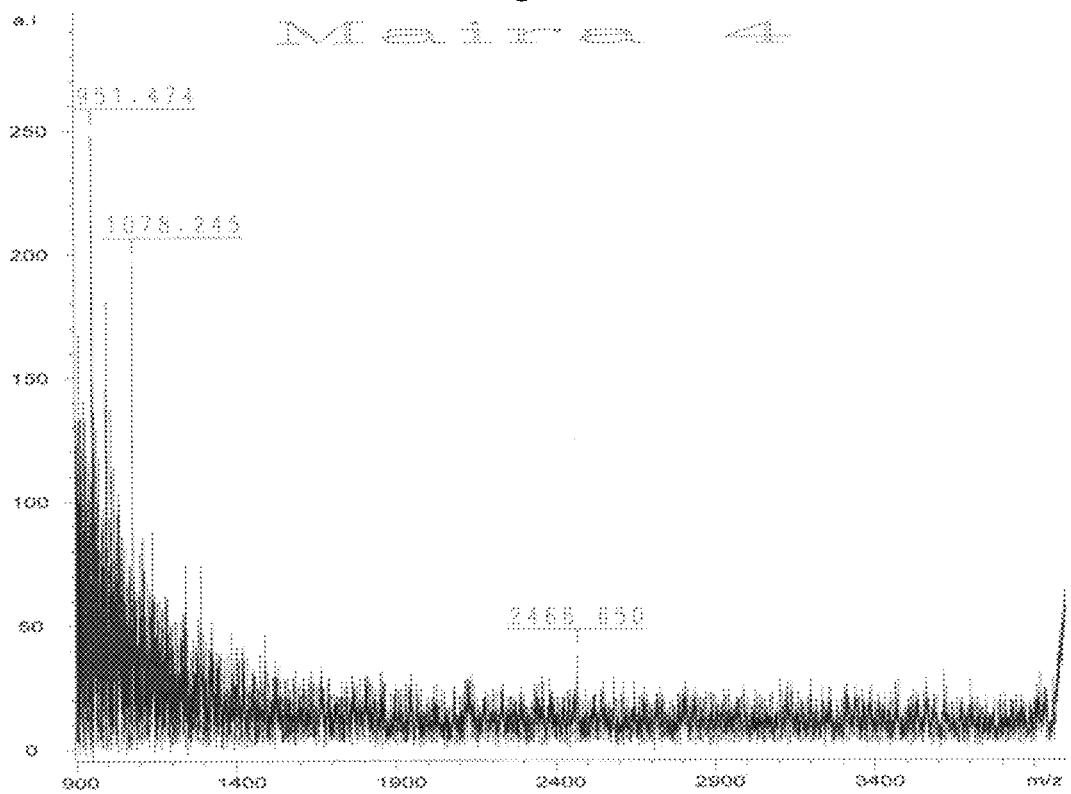
FIG. 13. LC-MS analysis of peptide peak 1 (Moira 4).
Figure 14:
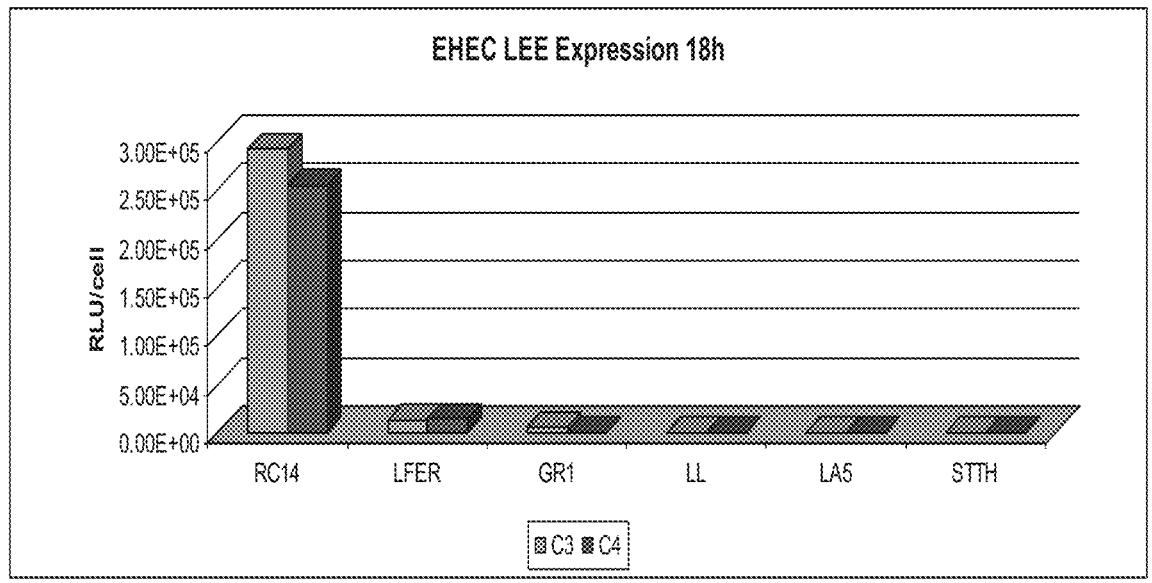
FIG. 14 *E. coli* O157:H7 construct C3 (LEE1::lux) and C4 (LEE2::lux) grown in LB broth supplemented with medium conditioned by the growth of probiotic LAB. Constructs grown in LB:MRS broth were used as positive controls (data not shown). Light induction is reported as relative light units (RLU) per cell.
Figure 15:
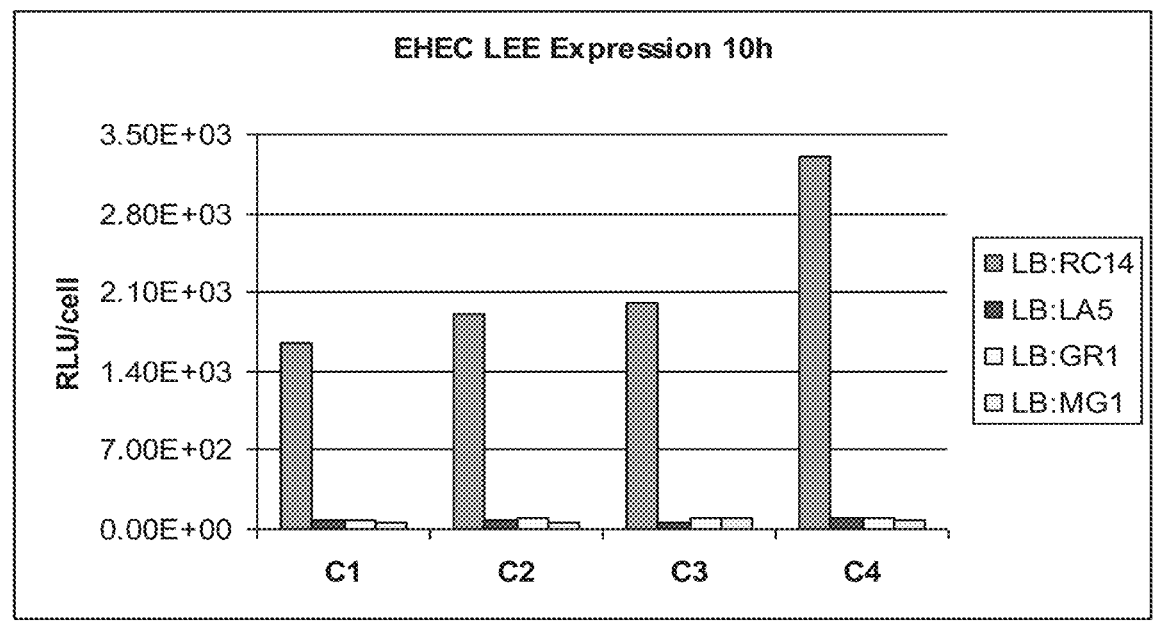
FIG. 15. *E. coli* O157:H7 construct C1 (LEE1::lux), C2 (LEE2::lux), C3 (LEE1::lux) and C4 (LEE2::lux) grown in LB broth supplemented with medium conditioned by the growth of probiotic LAB. Constructs grown in LB:MRS broth were used as positive controls (data not shown). Light induction is reported as relative light units (RLU) per cell.
Figure 16:
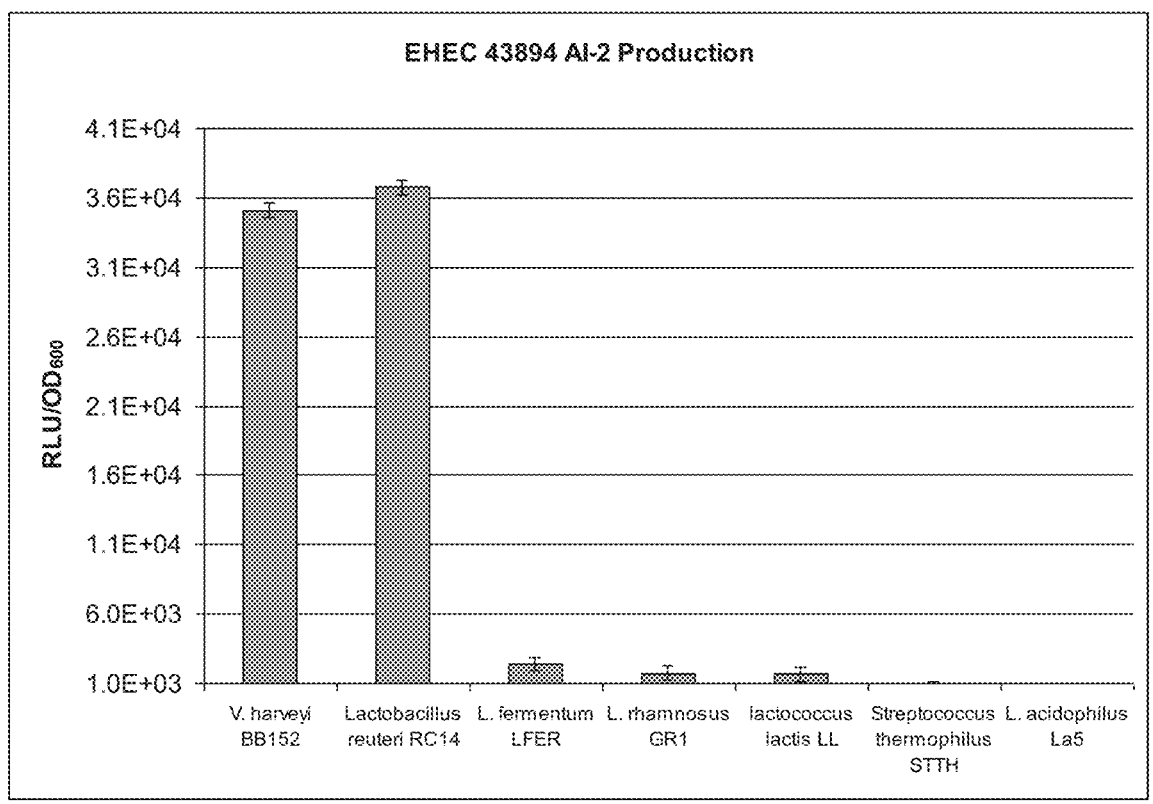
FIG. 16. AI-2 signaling molecule production as detected by the *V. harveyi* autoinducer-2 bioassay. EHEC O157:H7 strain 43894 was grown in LB broth supplemented with CFSM of probiotic LAB. Positive and negative controls were *V. harveyi* strain BB152 (+) and *E. coli* DH5α (−), respectively (negative control not shown). Results were expressed as relative light units (RLU) defined as counts min$^{-1}$ and adjusted to OD$_{600}$ (RLU/OD$_{600}$). The data are mean±SD values of three independent replicates of each sample.

Peptide peaks collected were concentrated and desalted before being sent for LC-MS analysis and peptide sequencing. Mass spectrometry was carried out using an Agilent HPLC, coupled to an Agilent 6110 single quadripole LC/MS (Agilent Technologies). The molar masses of three peptide peaks (FI, FIII and FIV) were detected at m/z 994, 997, 1019, 1078, 1139, 1289 and 2466. Peptide peak (FII) showed no signal peaks (FIGS. 11, 12 and 13), The peptide sequencing analysis of peaks FI, FII and FIV showed that the peptide fractions are composed of 4 to 6 amino acid residues (Table 10). There is a possibility that the amino acid sequences obtained are partial peptide sequences of larger peptides or small proteins due to possible blocked N-termini. Blocked N-termini provide the single largest impediment to protein sequence analysis. An estimated 50-80% of all proteins naturally have chemically modified N-termini. The sequential Edman analysis sequences the N-terminal and internal protein. In this process, the N-terminal amino acid is reacted with phenylisothiocyanate (PITC) to form a phenylthiocarbamyl (PTC) protein. The PTC protein is then cleaved with trifluoroacetic acid (TFA), resulting in the formation of an intermediate anilinothiazolinone (ATZ). The intermediate is converted to the more stable phenylthiohydantoin (PTH) amino acid derivative and subsequently separated by HPLC, compared against a standard, and identified by the sequencer software.

Example 10

Peptide Sequencing Analysis

| Sample | Amino acid residues | | | | | |
|---|---|---|---|---|---|---|
| Peptide peak (FI) | Y-Tyr | P-Pro | V-Val | E-Glu | P-Pro | F-Phe |
| Peptide peak (FIII) | A-Ala, Y-Tir$^a$, V-Val | P-Pro | P-Pro | G-Gly, Y-Tyr | G-Gly, Y-Tyr | P-Pro |
| Peptide peak (IV) | N-Asn, A-Ala, F-Phe | Q-Gln | P-Pro | Y-Tyr | | |

$^a$Amino acid most likely to be present at residue 1

BLAST analysis of the peptide sequences. The amino acid sequences of the peptide peaks were introduce in the Basic Local Alignment Search Tool (BLAST) and found a number of matches. BLASTp was done using default opening and gap penalties and a default scoring matrix. We will mention only the 100% homology (Table 5.4).

Proteins with 100% homology to the peptide peaks as determined by BLASTp using default opening and scouring matrix and default gap penalties.

| Peak sequence/ sequence aligned | BLASTp protein (100% homology to peptide sequence) |
|---|---|
| YPVEPF/YPVEPF | YP 194702 neopullulanase [*Lactobacillus acidophilus* NCFM] |
| YPPGGP/YPPG | YP 193877 ornithine decarboxylase chain A [*Lactobacillus acidophilus* NCFM] |
| NQPY/NQPY | YP 193484 glutamine ABC transporter [*Lactobacillus acidophilus* NCFM] |

TABLE 1

Bacterial strains and constructs used in this study

| Strain, plasmid, or construct | Serotype | Relevant genotype/property | Reference |
|---|---|---|---|
| Strains | | | |
| *E. coli* | | | |
| VS94 | O157:H7 | luxS negative | 21 |
| ATCC 43894 | O157:H7 | Stx1+ and Stx2+, isolated from human stool. Michigan, USA | CRIFS stock[a] |
| *L. acidophilus* | | | |
| La-5 | | Probiotic lactic acid bacteria | CRIFS stock[a] |
| Constructs | | | |
| *E. coli* | | | |
| ATCC 43894 (C4) | O157:H7 | Stx1+ and Stx2+, LEE2::lux | 15 |

[a]CRIFS stock strains are deposited in the Canadian Research Institute for Food Safety (CRIFS) culture collection.

TABLE 2

Adherence of EHEC O157 strains to HEp-2 cells.

| Bacteria | % Adherence[b] |
|---|---|
| EHEC 43894 | 100[a]* |
| EHEC 43894 coincubated with 10% *L. acidophilus* La5 fraction 33 | 26* |
| EHEC 43894 coincubated with 10% *L. acidophilus* La5 fraction 34 | 24* |
| EHEC VS94 luxS (−)ve + β-blocker | 22 |
| EHEC VS94 luxS (−)ve no β-blocker | 64 |

[a]EHEC 43894 control group CFU ml$^{-1}$ were normalized to 100% adherence ability.
[b]The results are average values of three independent replicates.
*Statistically significant value (P = 0.001 [student t test]).

TABLE 3

Areas of maximum bioluminescence in EHEC O157 infected mice calculated in terms of relative light unit counts per cm$^2$ per sec.

| | Mean Grey (cts [cm$^2$ s$^{-1}$]$^{-1}$)[a,b] |
|---|---|
| Mice experimental group | |
| EHEC 3$^{rd}$ day (control group) | 4002 ± 544[ns] |
| EHEC-probiotic 3rd day | 5171 ± 637[ns] |
| Probiotic-EHEC 3rd day | 4065 ± 884[ns] |
| EHEC 5$^{th}$ day (control group) | 21965 ± 4871* |
| EHEC-probiotic 5th day | 2176 ± 635* |
| Probiotic-EHEC 5th day | 792 ± 82* |
| EHEC 7$^{th}$ day (control group) | NA[c] |
| EHEC-Probiotic 7th day | 875 ± 172[c] |
| Probiotic-EHEC 7th day | 422 ± 1493[c] |
| Dose-response assay | |
| EHEC 10$^5$ 3$^{rd}$ day | 1900 ± 178 |
| EHEC 10$^6$ 3$^{rd}$ day | 2683.8 ± 65 |
| EHEC 10$^7$ 3$^{rd}$ day | 3364.85 ± 450 |
| EHEC 10$^8$ 3$^{rd}$ day | 5262.8 ± 391 |
| EHEC 10$^9$ 3$^{rd}$ day | 27998 ± 3059 |

[a]Areas of maximum bioluminescence were calculated in terms of relative light unit counts per cm$^2$ per sec (cts [cm$^2$ s$^{-1}$]$^{-1}$)
[b]The results are means ± standard deviations of three replicates.
[c]Control group did not survive to this point
*Statistically significant value (P < 0.05 [student t test])
[ns]Not statistically significant value (P > 0.05 [student t test])

TABLE 4

Mice average body conditioning scoring and survival rate 7 days after challenge with EHEC O157:H7.

| Mice experimental group | Body temperature (° C.)[a] | Rough hair coat (+/−)*[b] | Lethargic (+/−)*[b] | Survival rate by 5$^{th}$ day[b] |
|---|---|---|---|---|
| Group 1 (negative control) | 38.2 ± 0.17 | − | − | 5/5 |
| Group 2 (probiotic-EHEC) | 33.3 ± 1.7 | + | − | 5/5 |
| Group 3 (EHEC-probiotic) | 33.6 ± 1.3 | ++ | − | 5/5 |
| Group 4 (positive control) | 30.9 ± 1.3 | +++ | +++ | 2/5 |

[a]Data are means ± standard deviations of three group (n = 5) replicates
[b]Signs of deterioration and survival rate are averages of three group (n = 5) replicates
*(+) represents the presence of the sign of deterioration, (−) represents the absence of the sign of deterioration

TABLE 5

Bacterial strains and constructs used to study effects on hilA (luxCDABE::hilA)

| Strain, plasmid, or construct | Serotype | Relevant genotype/property | Reference |
|---|---|---|---|
| Strains | | | |
| *L. acidophilus* LA-5 | | Probiotic lactic acid bacteria | CRIFS stock[a] |
| *B. longum* | | Probiotic lactic acid bacteria | CRIFS stock[a] |
| *B. bifidum* | | Probiotic lactic acid bacteria | CRIFS stock[a] |
| *B. infantis* | | Probiotic lactic acid bacteria | CRIFS stock[a] |
| *B. crudilactis* | | Probiotic lactic acid bacteria | (Delcenserie et al., 2008) |
| Constructs | | | |
| *E. coli* | | | |
| ATCC 43888 (C1) | O157:H7 | Stx−, LEE1::lux | (Medellin-Pena et al., 2007) |

[a]CRIFS stock strains are deposited in the Canadian Research Institute for Food Safety (CRIFS) culture collection.

REFERENCES 1. 1993. Guide to the care and use of experimental animals. In C. C. o. A. Care (ed.), 2nd Edition ed, vol. 1 & 2.
2. Asahara, T., K. Shimizu, K. Nomoto, T. Hamabata, A. Ozawa, and Y. Takeda. 2004. Probiotic bifidobacteria protect mice from lethal infection with Shiga toxin-producing *Escherichia coli* O157:H7. Infect Immun 72:2240-7.
3. Beinke, C., S. Laarmann, C. Wachter, H. Karch, L. Greune, and M. A. Schmidt. 1998. Diffusely adhering *Escherichia coli* strains induce attaching and effacing phenotypes and secrete homologs of Esp proteins. Infect Immun 66:528-39.
4. Brovko, L. Y., C. Vandenende, B. Chu, K. Y. Ng, A. Brooks, and M. W. Griffiths. 2003. In vivo assessment of effect of fermented milk diet on course of infection in mice with bioluminescent *Salmonella*. J Food Prot 66:2160-3.
5. Clarke, M. B., and V. Sperandio. 2003. Presented at the 103rd American Society for Microbiology General Meeting, Washington, D.C., USA, May 18-22, 2003^_20030518.
6. Costa-Carvalho, B. T., A. Bertipaglia, D. Sole, C. K. Naspitz, and I. C. Scaletsky. 1994. Detection of immunoglobulin (IgG and IgA) anti-outer-membrane proteins of enteropathogenic *Escherichia coli* (EPEC) in saliva, colostrum, breast milk, serum, cord blood and amniotic fluid. Study of inhibition of localized adherence of EPEC to HeLa cells. Acta Paediatr 83:870-3.
7. Cravioto, A., A. Tello, H. Villafan, J. Ruiz, S. del Vedovo, and J. R. Neeser. 1991. Inhibition of localized adhesion of enteropathogenic *Escherichia coli* to HEp-2 cells by immunoglobulin and oligosaccharide fractions of human colostrum and breast milk. J Infect Dis 163:1247-55.
8. Donnenberg, M. S., J. B. Kaper, and B. B. Finlay. 1997. Interactions between enteropathogenic *Escherichia coli* and host epithelial cells. Trends Microbial 5:109-14.
9. Donnenberg, M. S., C. O. Tacket, S. P. James, G. Losonsky, J. P. Nataro, S. S. Wasserman, J. B. Kaper, and M. M. Levine. 1993. Role of the eaeA gene in experimental enteropathogenic *Escherichia coli* infection. J Clin Invest 92:1412-7.
10. Donnenberg, M. S., J. Yu, and J. B. Kaper. 1993. A second chromosomal gene necessary for intimate attachment of enteropathogenic *Escherichia coli* to epithelial cells. J Bacteriol 175:4670-80.
11. Gagnon, M., E. E. Kheadr, N. Dabour, D. Richard, and I. Fliss. 2006. Effect of *Bifidobacterium thermacidophilum* probiotic feeding on enterohemorrhagic *Escherichia coli* O157:H7 infection in BALB/c mice. Int J Food Microbiol 111:26-33.
12. Gansheroff, L. J., M. R. Wachtel, and A. D. O'Brien. 1999. Decreased adherence of enterohemorrhagic *Escherichia coli* to HEp-2 cells in the presence of antibodies that recognize the C-terminal region of intimin. Infect Immun 67:6409-17.
13. Gill, H. S., Q. Shu, H. Lin, K. J. Rutherfurd, and M. L. Cross. 2001. Protection against translocating *Salmonella typhimurium* infection in mice by feeding the immuno-enhancing probiotic *Lactobacillus rhamnosus* strain HN001. Med Microbiol Immunol 190:97-104.
14. Huebner, E. S., and C. M. Surawicz. 2006. Probiotics in the prevention and treatment of gastrointestinal infections. Gastroenterol Clin North Am 35:355-65.
15. Hutt, P., J. Shchepetova, K. Loivukene, T. Kullisaar, and M. Mikelsaar. 2006. Antagonistic activity of probiotic lactobacilli and *bifidobacteria* against entero- and uropathogens. J Appl Microbiol 100:1324-32.
16. Imase, K., A. Tanaka, K. Tokunaga, H. Sugano, H. Ishida, and S. Takahashi. 2007. *Lactobacillus reuteri* tablets suppress *Helicobacter pylori* infection—a double-blind randomised placebo-controlled cross-over clinical study. Kansenshogaku Zasshi 81:387-93.
17. Jarvis, K. G., J. A. Giron, A. E. Jerse, T. K. McDaniel, M. S. Donnenberg, and J. B. Kaper. 1995. Enteropathogenic *Escherichia coli* contains a putative type III secretion system necessary for the export of proteins involved in attaching and effacing lesion formation. Proc Natl Acad Sci USA 92:7996-8000.
18. Jarvis, K. G., and J. B. Kaper. 1996. Secretion of extracellular proteins by enterohemorrhagic *Escherichia coli* via a putative type III secretion system. Infect Immun 64:4826-9.
19. Jerse, A. E., J. Yu, B. D. Tall, and J. B. Kaper. 1990. A genetic locus of enteropathogenic *Escherichia coli* necessary for the production of attaching and effacing lesions on tissue culture cells. Proc Natl Acad Sci USA 87:7839-43.
20. Kendall, M. M., and V. Sperandio. 2007. Quorum sensing by enteric pathogens. Curr Opin Gastroenterol 23:10-5.
21. Kenny, B., and B. B. Finlay. 1995. Protein secretion by enteropathogenic *Escherichia coli* is essential for transducing signals to epithelial cells. Proc Natl Acad Sci USA 92:7991-5.
22. Knutton, S., T. Baldwin, P. H. Williams, and A. S. McNeish. 1989. Actin accumulation at sites of bacterial adhesion to tissue culture cells: basis of a new diagnostic test for enteropathogenic and enterohemorrhagic *Escherichia coli*. Infect Immun 57:1290-8.
23. Knutton, S., R. K. Shaw, R. P. Anantha, M. S. Donnenberg, and A. A. Zorgani. 1999. The type IV bundle-forming pilus of enteropathogenic *Escherichia coli* undergoes dramatic alterations in structure associated with bacterial adherence, aggregation and dispersal. Mol Microbiol 33:499-509.
24. Lai, L. C., L. A. Wainwright, K. D. Stone, and M. S. Donnenberg. 1997. A third secreted protein that is encoded by the enteropathogenic *Escherichia coli* pathogenicity island is required for transduction of signals and for attaching and effacing activities in host cells. Infect Immun 65:2211-7.
25. Mayville, P., G. Ji, R. Beavis, H. Yang, M. Goger, R. P. Novick, and T. W. Muir. 1999. Structure-activity analysis of synthetic autoinducing thiolactone peptides from *Staphylococcus aureus* responsible for virulence. Proc Natl Acad Sci USA 96:1218-23.
26. McKee, M. L., A. R. Melton-Celsa, R. A. Moxley, D. H. Francis, and A. D. O'Brien. 1995. Enterohemorrhagic *Escherichia coli* O157:H7 requires intimin to colonize the gnotobiotic pig intestine and to adhere to HEp-2 cells. Infect Immun 63:3739-44.
27. McKee, M. L., and A. D. O'Brien. 1995. Investigation of enterohemorrhagic *Escherichia coli* O157:H7 adherence characteristics and invasion potential reveals a new attachment pattern shared by intestinal *E. coli*. Infect Immun 63:2070-4.
28. McKee, M. L., and A. D. O'Brien. 1996. Truncated enterohemorrhagic *Escherichia coli* (EHEC) O157:H7 intimin (EaeA) fusion proteins promote adherence of EHEC strains to HEp-2 cells. Infect Immun 64:2225-33.
29. Medellin-Pena, M. J., H. Wang, R. Johnson, S. Anand, and M. W. Griffiths. 2007. Probiotics affect virulence-related gene expression in *Escherichia coli* O157:H7. Appl Environ Microbiol 73:4259-67.
30. Novak, J., and J. A. Katz. 2006. Probiotics and prebiotics for gastrointestinal infections. Curr Infect Dis Rep 8:103-9.
31. Shu, Q., and H. S. Gill. 2001. A dietary probiotic (*Bifidobacterium lactic* HN019) reduces the severity of *Escherichia coli* O157:H7 infection in mice. Med Microbiol Immunol 189:147-52.
32. Shu, Q., and H. S. Gill. 2002. Immune protection mediated by the probiotic *Lactobacillus rhamnosus* HN001 (DR20) against *Escherichia coli* O157:H7 infection in mice. FEMS Immunol Med Microbiol 34:59-64.
33. Snelling, A. M. 2005. Effects of probiotics on the gastrointestinal tract. Curr Opin Infect Dis 18:420-6.
34. Sperandio, V., J. L. Mellies, W. Nguyen, S. Shin, and J. B. Kaper. 1999. Quorum sensing controls expression of the type III secretion gene transcription and protein secretion in enterohemorrhagic and enteropathogenic *Escherichia coli*. Proceedings of the National Academy of Science, USA 96:15196-15201.
35. Sperandio, V., A. G. Torres, J. A. Girón, and J. B. Kaper. 2001. Quorum sensing is a global regulatory mechanism in enterohemorrhagic *Escherichia coli* O157:H7. Journal of Bacteriology 183:5187-5197.
36. Sperandio, V., A. G. Torres, B. Jarvis, J. P. Nataro, and J. B. Kaper. 2003. Bacteria-host communication: The language of hormones. Proceedings of the National Academy of Science, USA 100:8951-8956.
37. Tzipori, S., F. Gunner, M. S. Donnenberg, L. de Montigny, J. B. Kaper, and A. Donohue-Rolfe. 1995. The role of the eaeA gene in diarrhea and neurological complications in a gnotobiotic, piglet model of enterohemorrhagic *Escherichia coli* infection. Infect Immun 63:3621-7.
38. Vinderola, G., C. Matar, and G. Perdigon. 2007. Milk fermented by *Lactobacillus helveticus* R389 and its non-bacterial fraction confer enhanced protection against *Salmonella enteritidis* serovar *typhimurium* infection in mice. Immunobiology 212:107-18.
39. Bajaj, V., Lucas, R. L., Hwnag, C., and Lee, C. A. (1996) Co-ordinate Regulation of *Salmonella typhymurium* Invasion Genes by Environmental and Regulatory Factors is Mediated by Control of hilA Expression. *Molecular Microbiology* 22: 703-714.
40. Behlau, I., and Miller, S. I. (1993) A PhoP-repressed Gene Promotes *Salmonella typhimurium* Invasion of Epithelial Cells. *Journal of Bacteriology* 175: 4475-4484.
41. Chen, L., Kaniga, K., and Galan, J. (1996) *Salmonella* spp. are cytotoxic for cultured macrophages. *Molecular Microbiology* 21: 1101-1115.
43. Hueck, C. J. (1998) Type II Protein Secretion Systems in Bacterial Pathogenes of Animals and Plants. *Microbiology and Molecular Biology Reviews* 62: 379-433.
44. Kubori, T., Matsushima, Y., Nakamura, D., Uralil, J., Lara-Tejero, M., Sukhan, A., Galan, J., and Aizawa, S. (1998) Supramolecular structure of the *Salmonella typhimurium* Type III Protein Secretion System. *Science* 280: 602-605.
45. Lee, C. A., and Falkow, S. (1990) The Ability of *Salmonella* to Enter Mammalian Cells is Affected by Bacterial Growth State, *Proceedings of the National Academy of Sciences* 87: 4304-4308.
46. Lindgren, S. W., Stojiljkovic, 1, and Heffron, F. (1996) Macrophage Killing is an Essential Virulence Mechanism of *Salmonella typhimurium*. *Microbiology and Molecular Biology Reviews* 93: 4197-4201.
47. Monack, D. M., Raupach, B., Hromockyj, A. E., and Falkow, S. (1996) *Salmonella typhimurium* Invasion induces apoptosis in Infected Macrophages. *Microbiology and Molecular Biology Reviews* 93: 9833-9838.
48. (Threlfall, E. J. et al., Vet. Rec. 134:577 (1994).
49. Holzapfel W H, et al. Int J Food Microbial 1998 May 26; 41(2): 85-101.
50. von Wright, et al. Eur J Gastroenterol Hepatol 1999 November; 11(11): 1195-119.
51. Marteau, P R et al. Am J Clin Nutr February; 73(2 Suppl): 430S-436S.
52. Cummings J H, et al. Am Nutr 2001 February; 73(2 Suppl): 415S-420S.

The invention claimed is:

1. A method for attenuating virulence and/or treating an enteric *Salmonella* and/or *Escherichia coli* infection, the method comprising administering a composition comprising a peptide from *Lactobacillus acidophilus* strain La-5, wherein the peptide has from 2 to 10 amino acids and wherein the peptide is not a bacteriocin.

2. The method of claim 1, wherein the composition is effective against *Salmonella* and/or *Escherichia coli* colonization.

3. The method of claim 2, wherein said *Salmonella* is *Salmonella enterica* and said *Escherichia coli* is EHEC O157:H7.

4. The method of claim 1, wherein the composition further comprises an edible food product, a nutritional supplement, an ingestible liquid, one or more strains of whole probiotic bacteria, or combinations thereof.

5. The method of claim 1, wherein the peptide comprises an amino acid sequence selected from YPVEPF, YPPGGP, YPPG, NQPY, and combinations thereof.

6. The method of claim 1, wherein the composition further comprises a sugar source and/or one or more antibiotics.

7. The method of claim 6, wherein the sugar source comprises glucose.

8. The method of claim 1, wherein the composition comprises a supernatant from the probiotic bacteria.

9. The method of claim 8, wherein the supernatant is cell-free.

10. The method of claim 8, wherein the supernatant is concentrated.

11. The method of claim 10, wherein the supernatant is concentrated by lyophilization or spray-drying.

12. The method of claim 1 for reducing the carriage by a food production animal of bacterial strains that cause human disease.

* * * * *

UNITED STATES PATENT AND TRADEMARK OFFICE
CERTIFICATE OF CORRECTION

PATENT NO. : 10,687,543 B2  
APPLICATION NO. : 15/696255  
DATED : June 23, 2020  
INVENTOR(S) : Griffiths et al.

Page 1 of 2

It is certified that error appears in the above-identified patent and that said Letters Patent is hereby corrected as shown below:

In the Specification

Column 2, Line 62: Please correct "*O*157:H7" to read -- O157:H7 --

Column 4, Line 55: Please correct "in viva in" to read -- *in vivo* in --

Column 5, Line 57: Please correct "(Lo-5)" to read -- (La-5) --

Column 6, Line 52: Please correct "hilA" to read -- *hilA* --

Column 6, Line 55: Please correct "hilA" to read -- *hilA* --

Column 7, Line 28: Please correct "(Moira 4)." to read -- (Maira 4). --

Column 10, Line 22: Please correct "O257:H7" to read -- O157:H7 --

Column 10, Line 32: Please correct "O257:H7" to read -- O157:H7 --

Column 11, Line 11: Please correct "O257:H7" to read -- O157:H7 --

Column 13, Line 17: Please correct "O257:H7" to read -- O157:H7 --

Column 13, Line 29: Please correct "O257:1-17" to read -- O157:H7 --

Column 13, Line 38: Please correct "O257:H7" to read -- O157:H7 --

Column 14, Line 50: Please correct "1.0 g" to read -- 10 g --

Column 14, Line 54: Please correct "1. L" to read -- 1 L --

Signed and Sealed this  
Seventeenth Day of November, 2020

Andrei Iancu  
*Director of the United States Patent and Trademark Office*

CERTIFICATE OF CORRECTION (continued)
U.S. Pat. No. 10,687,543 B2

Column 14, Line 63: Please correct "La-S" to read -- La-5 --

Column 16, Line 44: Please correct "O257:H7" to read -- O157:H7 --

SEQUENCE LISTING

```
<160> NUMBER OF SEQ ID NOS: 4

<210> SEQ ID NO 1
<211> LENGTH: 6
<212> TYPE: PRT
<213> ORGANISM: Lactobacillus acidophilus

<400> SEQUENCE: 1

Tyr Pro Val Glu Pro Phe
1               5

<210> SEQ ID NO 2
<211> LENGTH: 6
<212> TYPE: PRT
<213> ORGANISM: Lactobacillus acidophilus

<400> SEQUENCE: 2

Tyr Pro Pro Gly Gly Pro
1               5

<210> SEQ ID NO 3
<211> LENGTH: 4
<212> TYPE: PRT
<213> ORGANISM: Lactobacillus acidophilus
```

```
<400> SEQUENCE: 3

Tyr Pro Pro Gly
1

<210> SEQ ID NO 4
<211> LENGTH: 4
<212> TYPE: PRT
<213> ORGANISM: Lactobacillus acidophilus

<400> SEQUENCE: 4

Asn Gln Pro Tyr
1
```